United States Patent
Eckert et al.

(10) Patent No.: US 12,311,037 B2
(45) Date of Patent: May 27, 2025

(54) DENTAL COMPOSITION CONTAINING A RESORCINOL OR CATECHOL MOIETY CONTAINING COMPONENT AND USE THEREOF

(71) Applicant: Solventum Intellectual Properties Company, Maplewood, MN (US)

(72) Inventors: Adrian S. Eckert, Herrsching (DE); Christoph H. Thalacker, Weilheim (DE); Karsten Dede, Landsberg am Lech (DE); Marion B. Kandlbinder, Munich (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/853,771

(22) PCT Filed: Mar. 29, 2023

(86) PCT No.: PCT/IB2023/053134
§ 371 (c)(1),
(2) Date: Oct. 3, 2024

(87) PCT Pub. No.: WO2023/209463
PCT Pub. Date: Nov. 2, 2023

(65) Prior Publication Data
US 2025/0114283 A1    Apr. 10, 2025

(30) Foreign Application Priority Data

Apr. 26, 2022 (EP) .................... 22169878

(51) Int. Cl.
*A61K 6/00* (2020.01)
*A61K 6/30* (2020.01)
*A61K 6/62* (2020.01)
*A61K 6/891* (2020.01)

(52) U.S. Cl.
CPC .............. *A61K 6/891* (2020.01); *A61K 6/62* (2020.01)

(58) Field of Classification Search
None
See application file for complete search history.

(56) References Cited

U.S. PATENT DOCUMENTS

| | | |
|---|---|---|
| 3,729,313 A | 4/1973 | Smith |
| 3,741,769 A | 6/1973 | Smith |
| 3,808,006 A | 4/1974 | Smith |
| 3,853,962 A | 12/1974 | Gander |
| 4,250,053 A | 2/1981 | Smith |
| 4,394,403 A | 7/1983 | Smith |
| 4,642,126 A | 2/1987 | Zador et al. |
| 4,652,274 A | 3/1987 | Boettcher et al. |
| 4,737,593 A | 4/1988 | Ellrich et al. |
| 4,744,827 A | 5/1988 | Winkel |
| 4,772,530 A | 9/1988 | Gottschalk et al. |
| 4,874,450 A | 10/1989 | Gottschalk |
| 4,954,414 A | 9/1990 | Adair et al. |
| 5,055,372 A | 10/1991 | Shanklin |
| 5,057,393 A | 10/1991 | Shanklin et al. |
| 5,545,676 A | 8/1996 | Palazzotto et al. |
| 5,624,260 A | 4/1997 | Wilcox |
| 5,750,589 A | 5/1998 | Zech |
| 5,865,803 A | 2/1999 | Major |
| 5,927,562 A | 7/1999 | Hammen et al. |
| 5,998,495 A | 12/1999 | Oxman |
| 6,025,406 A | 2/2000 | Oxman |
| 6,043,295 A | 3/2000 | Oxman |
| 6,084,004 A | 7/2000 | Weinmann et al. |
| 6,126,922 A | 10/2000 | Rozzi et al. |
| 6,187,833 B1 | 2/2001 | Oxman et al. |
| 6,444,725 B1 | 9/2002 | Trom et al. |
| 6,572,693 B1 | 6/2003 | Wu et al. |
| 6,730,156 B1 | 5/2004 | Windisch et al. |
| 6,765,036 B2 | 7/2004 | Dede et al. |
| 6,899,948 B2 | 5/2005 | Zhang et al. |
| 8,314,162 B2 | 11/2012 | Hailand |
| 8,426,490 B2 | 4/2013 | Bissinger |
| 9,056,043 B2 | 6/2015 | Joly et al. |
| 9,295,617 B2 * | 3/2016 | Eckert ................ A61K 6/00 |
| 10,231,810 B2 | 3/2019 | Gramann |
| 10,758,126 B2 | 9/2020 | Geldmacher |
| 2007/0172789 A1 | 7/2007 | Muller |
| 2010/0076115 A1 | 3/2010 | Utterodt |
| 2011/0151403 A1 | 6/2011 | Pauser |
| 2011/0315928 A1 | 12/2011 | Jin |

(Continued)

FOREIGN PATENT DOCUMENTS

| EP | 1340472 A1 | 9/2003 |
|---|---|---|
| WO | 2000069393 A1 | 11/2000 |

(Continued)

OTHER PUBLICATIONS

Extended EP Search Report for EP Application No. 22169878.0, mailed on Oct. 10, 2022, 7 pages.
International Search Report for PCT International Application No. PCT/IB2023/053134 mailed on May 15, 2023, 4 pages.
Watts, D.C, and A.J Cash. "Determination of Polymerization Shrinkage Kinetics in Visible-Light-Cured Materials: Methods Development." Dental materials 7.4 (1991): 281-287.

*Primary Examiner* — Tae H Yoon

(57) ABSTRACT

The invention relates to a composition comprising a resin matrix, an initiator system and a filler system. The resin matrix comprises a polymerizable component which contains a backbone comprising either a resorcinol or catechol moiety. The composition is in particular useful in the dental and orthodontic field, e.g. as dental filling material having advantageous properties.

12 Claims, No Drawings

(56) References Cited

U.S. PATENT DOCUMENTS

| | | |
|---|---|---|
| 2017/0065495 A1 | 3/2017 | Eckert et al. |
| 2020/0069532 A1 | 3/2020 | Thalacker et al. |
| 2021/0113301 A1 | 4/2021 | Pauser |

FOREIGN PATENT DOCUMENTS

| | | |
|---|---|---|
| WO | 2012106083 A1 | 8/2012 |
| WO | 2019092581 A1 | 5/2019 |

* cited by examiner

DENTAL COMPOSITION CONTAINING A RESORCINOL OR CATECHOL MOIETY CONTAINING COMPONENT AND USE THEREOF

CROSS REFERENCE TO RELATED APPLICATIONS

This application is a national stage filing under 35 U.S.C. 371 of PCT/IB2023/053134, filed Mar. 29, 2023, which claims the benefit of EP Application No. 22169878, filed Apr. 26, 2022, the disclosure of which is incorporated by reference in their entirety herein.

FIELD OF INVENTION

The invention relates to a composition comprising a resin matrix, an initiator system and a filler system. The resin matrix comprises a polymerizable component which contains a backbone comprising either a resorcinol or catechol moiety.

The composition is in particular useful in the dental and orthodontic field, e.g. as dental filling material having advantageous properties.

The dental composition can also be used for producing mill blanks and as resin in an additive-manufacturing method.

BACKGROUND

Different dental filling materials for restorative purposes are known, including amalgam and dental composite materials.

In order to fulfil its main function (replacement of lost tooth structure), dental filling materials need to have adequate physical properties. In particular, they have to have sufficient strength to be able to absorb and resist chewing forces.

If, however, the material is too hard, it will also become more brittle.

Thus, a dental filling material not only needs to be sufficiently hard, but also needs to be to some extend flexible.

To address these needs, commercially available dental composite filling materials typically contain a certain amounts of resin matrix, filler and initiator.

A widely used polymerizable (meth)acrylate component contained in the resin matrix is bisphenol A-glycidyl methacrylate (Bis-GMA) or other bisphenol based (meth)acrylate monomers.

Compositions containing bisphenol-based monomers are said to have a variety of advantageous properties like high compressive strength, thus enabling the practitioner to formulate a variety of different dental compositions for restorative purposes.

Some literature, however, seems to indicate that bisphenol-based monomers are not always recommended for all purposes. Alternative polymerizable (meth)acrylate components are thus needed.

US 2010/076115 A1 (Heraeus Kulzer) relates to compositions for dental composites comprising acrylic acid esters of tricyclo[5.2.1.02.6]decane with urethane groups.

U.S. Pat. No. 3,853,962 (Gander) relates to dental restorative cements comprising the methacrylate monomer 1,3-bis [2-,3-di(methacryloxy)-propoxy]-benzene. Restorative compositions containing this kind of monomer are said to have improved compressive strength and related physical properties.

U.S. Pat. No. 4,744,827 (Winkel) describes (meth)acrylic acid derivatives of a tricyclodecane exhibiting considerably less polymerization shrinkage.

U.S. Pat. No. 8,426,490 B2 (Bissinger et al.) describers methacrylate based monomers containing a urethane linkage showing well-balanced properties with respect to viscosity, refractive index, molecular weight and shrinkage value.

US 2011/0315928 A1 (Jin at al.) relates to a low viscosity and low stress dental composition comprising at least one low stress polymerizable resin and at least one filler. The dental composition are said to have high depth of cure and self-levelling characteristics and are capable of bulk application.

WO 2012/106083 A1 (3M) describes a dental composition comprising a hardenable compound which contains a comparable rigid backbone unit comprising an aromatic or an aliphatic cyclic moiety, a spacer unit and a unit comprising polymerizable end groups. The composition is useful in the dental field for providing e.g. composite materials with reduced brittleness.

SUMMARY OF INVENTION

There is still a need for a composition which can be used in the dental and orthodontic field with improved properties.

The composition should be easy to handle in its uncured state, in particular easy to apply to a surface to be treated.

It would also be desirable, if the composition allows for a high filler loading, if desired.

These properties should be achievable without the need of using bisphenol-A (BPA) containing monomers.

Ideally, after hardening the composition the composition should have adequate physical-mechanical properties, such as sufficient flexural strength and depth of cure.

Further, if possible, for achieving the desired aesthetics and depth of cure properties, the polymerizable component(s) of the curable composition should have an adequate refractive index.

One or more of these objectives are achieve by the invention described in the present text and claims.

In one embodiment the present invention features a dental composition comprising a) a resin matrix, b) an initiator system, c) a filler system, the resin matrix comprising a polymerizable component A1 being characterized by either of the following formulas I, II or III (I)

-continued (II)

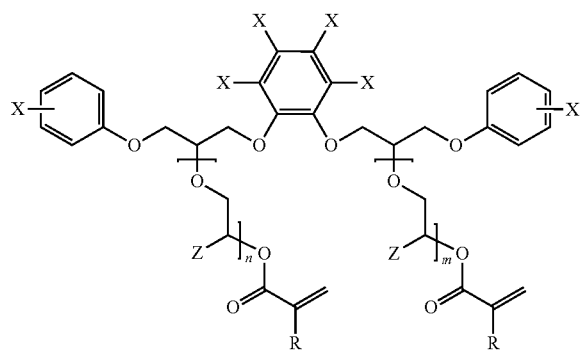

with
X=independently selected from H, alkyl, I, Br, Cl;
Z=independently selected from H, CH$_3$, CH$_2$OH; n,
m=independently selected from an integer in the range of 1 to 10; (m+n)=1 to 10 or 2 to 8 or 2 to 6;
R=independently selected from H, CH$_3$;

(III)

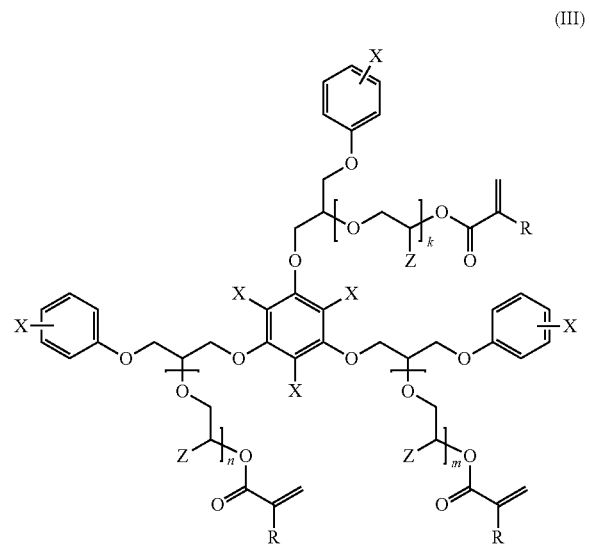

with X=independently selected from H, alkyl, I, Br, Cl;
Z=independently selected from H, CH$_3$, CH$_2$OH; k, n,
m=independently selected from an integer in the range of 1 to 10; (k+m+n)=1 to 15, or 2 to 10, or 3 to 8;
R=independently selected from H, CH$_3$;
and mixtures thereof as described in the present text and claims.

A further embodiment of the invention is directed to a kit of parts comprising the dental composition as described in the present text and claims and the following items alone or in combination: dental adhesive; dental primer; dispensing device; polishing equipment; dental curing light as described in the present text and claims.

The dental composition described in the present text can also be used for producing a dental restoration, a dental mill blank or as resin in an additive-manufacturing method as described in the present text and claims.

The dental composition can also be used as composite filling material, fixing material for orthodontic appliances, cavity liner, or sealant.

In another embodiment, the invention relates to the dental composition for use in a method of treating hard dental tissue in the mouth of a mammal, the method comprising the steps of applying the dental composition to the surface of hard dental tissue and hardening the dental composition as described in the present text and claims.

Described is also a packaging device comprising the composition described in the present text and claims.

Unless defined differently, for this description the following terms shall have the given meaning:

A "hardenable or curable or polymerizable component" is any component which can be cured or solidified by a hardening reaction, in particular in the presence of a photo-initiator by radiation-induced polymerization. A hardenable component may contain only one, two, three or more polymerizable groups. Typical examples of polymerizable groups include unsaturated carbon groups, such as a vinyl group being present i.a. in a (methyl)acrylate group.

As used herein, "hardening" or "curing" a composition are used interchangeably and refer to polymerization and/or crosslinking reactions including, for example, photo-polymerization reactions and chemical-polymerization techniques (e. g., ionic reactions or chemical reactions forming radicals effective to polymerize ethylenically unsaturated compounds) involving one or more materials included in the composition.

"Radiation curable" shall mean that the component (or composition, as the case may be) can be cured by applying radiation, preferably electromagnetic radiation with a wavelength in the visible light spectrum under ambient conditions and within a reasonable time frame (e.g. within about 15, 10 or 5 min).

The term "visible light" is used to refer to light having a wavelength of 400 to 700 nano meters (nm).

As used herein, "(meth)acryl" is a shorthand term referring to "acryl" and/or "methacryl". For example, a "(meth) acryloxy" group is a shorthand term referring to either an acryloxy group (i.e., CH$_2$=CH—C(O)—O—) and/or a methacryloxy group (i.e., CH$_2$=C(CH$_3$)—C(O)—O—).

A "resin matrix" contains all hardenable compounds (monomers, oligomers and/or polymers) being present in the hardenable composition. The resin may contain only one hardenable compound or a mixture of different hardenable compounds.

A "filler system" contains all fillers being present in the hardenable composition. Only one type of filler or a mixture of different fillers can be used.

A "nano-sized filler" is a filler, the individual particles thereof have a size in the region of nanometers, e.g. an average particle diameter of less than 100 nm or less than 50 nm. Useful examples are given in U.S. Pat. No. 6,899,948 (Zhang et al.) and U.S. Pat. No. 6,572,693 (Wu et al.).

A "particle" means a substance being a solid having a shape which can be geometrically determined. The shape can be regular or irregular. Particles can typically be analysed with respect to e.g. particle size and particle size distribution.

"Aggregated," as used herein, is descriptive of a strong association of particles often bound together by, for example, residual chemicals treatment or partially sintering. The specific surface of aggregated particles is typically smaller than the specific surface of the primary particles the aggregate is made of (cf. DIN 53206; 1972).

An "initiator or initiator system" is a component or a combination of components being able to start the curing process of a hardenable component.

"Dispersed within the resin" means that filler particles are present in the resin as discrete, non-associated (i.e. non-agglomerated and non-aggregated) particles.

A "dental composition" is any composition which can or is to be used in the dental area. In this respect the composition should be not detrimental to the patients' health and thus free of hazardous and toxic components being able to migrate out of the composition.

Possible uses for a dental composition are the use as or for producing permanent and temporary crown and bridge materials, artificial crowns, dental filling materials, cavity liners, coating compositions, sealants, mill blanks, lab materials and orthodontic devices.

Dental compositions are typically hardenable compositions, which can be hardened at ambient conditions, including a temperature range of 15 to 50° C. or 20 to 40° C. within a time frame of 30 min or 20 min or 10 min.

Higher temperatures are not recommended as they might cause pain to the patient and may be detrimental to the patient's health.

Dental compositions are typically provided to the practitioner in comparable small volumes, that is volumes in the range of 0.1 to 100 ml or 0.5 to 50 ml or 1 to 30 ml.

"Dental article" means an article which is to be used in the dental field, especially as or for producing a dental restoration. A dental article has typically two different surface portions, an outer surface and an inner surface. The outer surface is the surface which is typically not in permanent contact with the surface of a tooth. In contrast thereto, the inner surface is the surface which is used for attaching or fixing the dental article to a tooth. If the dental article has the shape of a dental crown, the inner surface has typically a concave shape, whereas the outer surface has typically a convex shape. A dental article should not contain components which are detrimental to the patient's health and thus free of hazardous and toxic components being able to migrate out of the dental or orthodontic article.

"Dental restoration" means dental articles which are used for restoring a tooth to be treated. Examples of dental restorations include crowns, bridges, inlays, onlays, veneers, facings, copings, crown and bridged framework, and parts thereof.

By "dental mill blank" is meant a solid block (3-dim article) of material from which a dental article can be machined. A dental milling block has typically a geometrically defined shape. A dental milling block may have a size of 20 mm to 30 mm in two dimensions, for example may have a diameter in that range, and may be of a certain length in a third dimension. A block or blank for making a single crown may have a length of 15 mm to 30 mm, and a block or blank for making bridges may have a length of 40 mm to 80 mm.

Besides the above-mentioned dimensions, a dental milling block may also have the shape of a cube, a cylinder or a cuboid. Larger milling blocks may be advantageous if more than one crown or bridge should be manufactured out of one blank. For these cases, the diameter or length of a cylindric or cuboid shaped mill blank may be in a range of 80 to 200 mm, with a thickness being in the range of 10 to 30 mm.

"Orthodontic appliance" includes orthodontic brackets, buccal tubes, lingual retainers, orthodontic bands, bite openers, buttons, and cleats.

"Additive manufacturing" or "3d-printing" means processes comprising a layer-wise creation of an object from digital data. The articles can be of almost any shape or geometry and are produced from a 3-dimensional model or other electronic data source.

Many 3d-printing technologies exist, one of them being vat polymerization which uses a radiation curing step to make 3-dimensional articles. Examples of vat polymerization techniques include stereolithography (SLA) and digital light processing (DLP).

"Stereolithography" is an example of an additive manufacturing technique where typically two motors are used for aiming a laser beam across the print area thereby solidifying the printing resin. This process breaks down the design, layer by layer, into a series of points.

"Digital light processing" is another example of an additive manufacturing technique and typically comprises the use of a digital projector screen to flash an image of each layer across the building platform of the additive manufacturing unit. The image is typically composed of square pixels, resulting in a layer formed from small rectangular bricks called voxels.

"Ambient conditions" mean the conditions which the composition described in the present text is usually subjected to during storage and handling. Ambient conditions may, for example, be a pressure of 900 to 1,100 mbar, a temperature of 10 to 40° C. and a relative humidity of 10 to 100%. In the laboratory ambient conditions are typically adjusted to 20 to 25° C. and 1,000 to 1,025 mbar (at maritime level).

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

The terms "comprise" or "contain" and variations thereof do not have a limiting meaning where these terms appear in the description and claims. "Consisting essentially of" means that specific further components can be present, namely those which do not materially affect the essential characteristic of the article or composition. "Consisting of" means that no further components should be present. The term "comprise" shall include also the terms "consist essentially of" and "consists of".

A composition is "essentially or substantially free of" a certain component, if the composition does not contain said component as an essential feature. Thus, said component is not willfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used. "Essentially free of" typically means a content of less than 1, 0.5 or 0.1 wt. %.

DETAILED DESCRIPTION

It has been found that the composition and processes described in the present text have a couple of advantageous properties.

The di- and/or tri-functional (meth)acrylate components show a high refractive index combined with a rather low viscosity.

A high refractive index may contribute to the curing properties and the aesthetics of the dental composition after curing.

Due to the low viscosity, these (meth)acrylate components can easily be incorporated into a resin matrix and mixed with other components such as fillers, even if at a high filling rate.

Formulating a low-viscous, flowable composition is now possible.

Further, it was found that these components are suitable substitutes for bis-phenol A derived components, which are often used in dental formulations. Bis-phenol A derived components means components containing a bis-phenol A moiety.

Compositions containing these components show favourable mechanical properties, such as low polymerization shrinkage stress, improved tensile and flexural strength and a sufficient depth of cure.

The composition also showed favourable cusp deflection values (i.e. low deformation of an aluminum block upon curing of a standardized filling) after curing.

The invention relates to a composition which can be used in the dental and orthodontic field.

The composition comprises a resin matrix, an initiator system, a filler system and optionally further components such as diluents and adjuvants.

The resin matrix comprises polymerizable component A1 and may comprise further polymerizable components being different from polymerizable component A1.

It was found that component A1 typically contributes to or shows at least one or more of the following properties.

Component A1
  a) typically has a good filler wettability. This may be beneficial to achieve comparably high filler loads, if desired;
  b) typically has a comparably low viscosity (e.g. 2.0 to 40 Pa*s, or 2.0 to 30 Pa*s; 23° C.; shear rate: 100 s$^{-1}$). This may be beneficial for achieving appropriate handling of the final composition, if desired. It can also be beneficial to increase the filler load, if desired, as the viscosity of the final composition will typically be in an acceptable range;
  c) typically has a comparably high refractive index (e.g. 1.520 to 1.565 or 1.530 to 1.560 ($n_D^{20}$)). This may be beneficial for achieving appropriate aesthetics and/or high depth of cure for light curing materials, if desired;
  d) typically has a comparably high hydrophobicity. This may be beneficial to achieve comparably low water uptake and/or exogenic staining, if desired;
  e) can be used to provide compositions showing reduced brittleness of the cured composition (i.e. a comparably high impact strength and/or a medium E-modulus). This may be beneficial if the risk of failures due to cracks and/or breaking should be reduced.
  f) can be used to provide compositions showing high depth of cure. This may be beneficial if a bulk cure application of light curing materials is desired.

Component A1 can be described as a component comprising a backbone unit comprising a di- or trihydroxybenzene moiety; and two or three spacer units being connected to the backbone unit via an ether linkage, the spacer units comprising the structural element —CH$_2$—CH—CH$_2$—; comprising two or three (meth)acrylate moieties, the (meth)acrylate moieties being attached to the backbone via alkylideneoxy moieties; comprising two or three phenoxy moieties as side groups attached to the backbone through the spacer units; and not comprising a urethane moiety.

The molecular weight of Component A1 is typically in a range of 500 to 1,200 g/mol. Examples of component A1 include

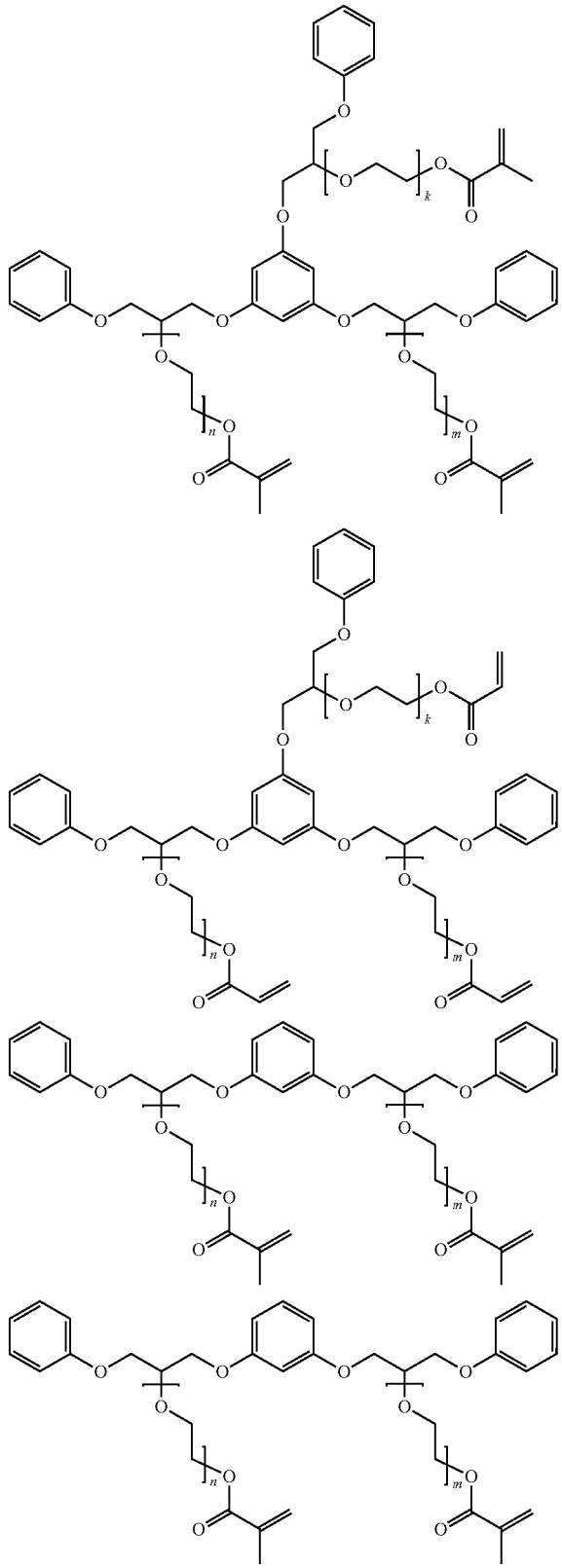

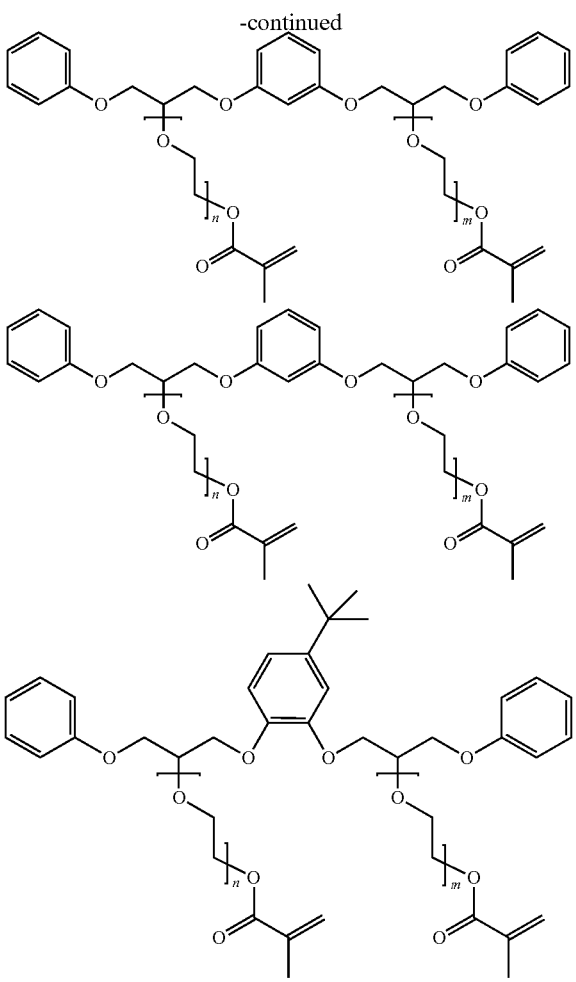

with m, n, k=being independently selected from an integer in the range of 1 to 10, and (m+n)=1 to 10, or (m+n+k)=1 to 15 and mixtures thereof.

The molecules of component A1 can generally be produced by reacting a phenolic compound (e.g. resorcinol or catechol), glycidyl phenyl ether compound, and ethylene carbonate to yield an alkoxylated intermediate compound, which is hydrolyzed to yield an ethoxylated intermediate compound, which is further reacted with (meth)acrylic acid.

Component A1 is typically present in the composition in the following amounts: at least 3, 5 or 8 wt. %; at most 50, 40 or 30 wt. %; range of 3 to 50, or 5 to 40, or 8 to 30 wt. %; wt. % with respect to the weight of the whole composition.

The resin matrix may comprise further polymerizable components being different from component A1. One or more of those further polymerizable components may be present.

These further polymerizable components are referred to as component A2.

Suitable components A2 contain at least one ethylenically unsaturated bond and are capable of undergoing addition polymerization.

Suitable polymerizable components can be characterized by the following formula:

$$A_nBA_m,$$

with A being an ethylenically unsaturated group, such as a (meth)acryl moiety,

B being selected from (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or poly-acrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, 1,6 hexandiol di(meth)acrylate, 1,10 decanediol di(meth)acrylate, 1,12 dodecanediol di(meth)acrylate, trimethylolpropane tri(meth)acrylate, 1,2,4-butanetriol tri(meth)acrylate, 1,4-cyclohexanediol di(meth)acrylate, pentaerythritol tri (meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, and trishydroxyethyl-isocyanurate trimethacrylate; the bis-acrylates and bis-methacrylates of polyethylene glycols of molecular weight 200 to 500, copolymerizable mixtures of acrylated monomers (see e.g. U.S. Pat. No. 4,652,274), and acrylated oligomers (see e.g. U.S. Pat. No. 4,642,126); and vinyl compounds such as styrene, divinyl succinate, divinyl adipate and divinylphthalate; polyfunctional (meth)acrylates comprising urethane, urea or amide groups. Mixtures of two or more of these free radically polymerizable materials can be used if desired.

If desired, addition fragmentation monomers (AFM) may also be added. Addition fragmentation monomers can be characterized by the following formula:

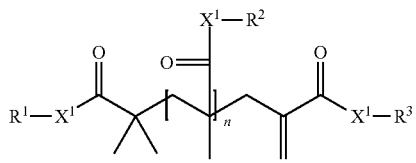

wherein $R^1$, $R^2$ and $R^3$ are each independently $Z_m$-Q-, a (hetero)alkyl group or a (hetero)aryl group with the proviso that at least one of $R^1$, $R^2$ and $R^3$ is $Z_m$-Q-; Q is a linking group have a valence of m+1; Z is an ethylenically unsaturated polymerizable group; m is 1 to 6; each $X^1$ is independently —O— or —$NR^4$—, where $R^4$ is H or $C_1$-$C_4$ alkyl; and n is 0 or 1.

These monomers are said to lower stress. Suitable monomers are also described in U.S. Pat. No. 9,056,043 (Joly et al.).

Monomers comprising a hydroxyl moiety can also be added. Suitable compounds include 2-hydroxyethyl (meth) acrylate (HEMA), 2- or 3-hydroxypropyl (meth)acrylate, 4-hydroxybutyl (meth)acrylate, 5-hydroxypentyl (meth) acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono-(meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di (meth)acrylate, 3-hydroxypropyl-1,2-di(meth)acrylate, N-(meth)acryloyl-1,2-dihydroxypropylamine, N-(meth) acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, 2-hydroxyethyl (meth)acrylate, 2-hydroxypropyl (meth)acrylate and 2,3-dihydroxypropyl (meth)acrylate are particularly preferable. If desired, mixtures of one or more of these components can be used.

Component A2 is typically present in the composition in the following amounts: at least 0, 1, or 5 wt. %; at most: 60, 50 or 40 wt. %; range of 0 to 60, 1 to 50 or 5 to 40 wt. %; wt. % with respect to the whole composition.

The composition described in the present text comprises an initiator system.

The initiator system is able to start the curing process of the hardenable components being present in the resin matrix. For curing one-part compositions typically a photo-initiator system is used.

Suitable photo-initiator systems for free radical polymerization are generally known to the person skilled in the art dealing with dental materials.

Suitable photo-initiator systems often contain a sensitizer comprising alpha-alpha di-keto moiety, an anthraquinone moiety, a thioxanthone moiety or benzoin moiety. Sensitizers containing an alpha-alpha di-keto moiety are often preferred.

Typical photo-initiator systems comprise a combination of a sensitizer and a reducing agent or donor component, which is often referred to as photo-initiator system.

As sensitizer, those which can polymerize the polymerizable monomer(s) by the action of a visible light having a wavelength of from 390 nm to 830 nm are preferred.

Examples of sensitizers which can be used include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, I-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

As the reducing agent or donor component, tertiary amines and the like are generally used. Suitable examples of the tertiary amines include N,N-dimethyl-p-toluidine, N,N-dimethyl-aminoethyl methacrylate, triethanolamine, methyl 4-dimethylaminobenzoate, ethyl 4-dimethyl-aminobenzoate, methyldiphenylamine and isoamyl 4-dimethylaminobenzoate.

Further suitable reducing agents include diarylalkylamines characterized by the following formula $Ar^1Ar^2RN$, with $Ar^1$ and $Ar^2$ being independently selected from phenyl or alkyl (e.g. $C_1$ to $C_4$) substituted phenyl, R being an alkyl (e.g. $C_1$ to $C_4$) group wherein one or more H atoms can be substituted by halogen and N being nitrogen. These reducing agents are described in more detail in U.S. Pat. No. 8,314,162 (Hailand et al.).

Moreover, ternary photopolymerization initiating systems consisting of a sensitizer, an electron donor and an onium salt as described in U.S. Pat. No. 6,187,833 (Oxman et al.), U.S. Pat. No. 6,025,406 (Oxman et al.), U.S. Pat. No. 6,043,295 (Oxman et al.), U.S. Pat. No. 5,998,495 (Oxman et al.), U.S. Pat. No. 6,084,004 (Weinmann et al.), U.S. Pat. No. 5,545,676 (Palazzotto et al.) and U.S. Pat. No. 8,314,162 B2 (Hailand et al.) and U.S. Pat. No. 6,765,036 (Dede et al.) can be used.

In the ternary photo-initiator system, the first component is an onium, preferably an iodonium salt, i.e., a diaryliodonium salt.

The iodonium salt is preferably soluble in the monomer and storage stable (i. e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403. The iodonium salt can be a simple salt (e.g., containing an anion such as $Cl^-$, $Br^-$, $I^-$ or $C_4H_5 SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photo-initiator system is a sensitizer.

The sensitizer desirably is soluble in the monomer and is capable of light absorption within the range of wavelengths of greater than 400 to 1,200 nm, more preferably greater than 400 to 700 nm and most preferably greater than 400 to 600 nm.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers.

For example, a preferred class of ketone sensitizers has the formula: $ACO(X)_b$ B, where X is CO or $CR^5 R^6$, where $R^5$ and $R^6$ can be the same or different, and can be hydrogen, alkyl, alkaryl or aralkyl, b is zero or one, and A and B different and can be substituted (having one or more non-interfering substituents) can be the same or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone and the like.

The third component of a ternary initiator system is a donor.

Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676. This reference is incorporated herein by reference.

Alternatively, free-radical initiators useful in the invention include the class of acylphosphine oxides and bisacylphosphine oxides.

Suitable acylphosphine oxides can be described by the general formula

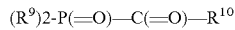
$(R^9)_2-P(=O)-C(=O)-R^{10}$ wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Examples can also be found e.g. in U.S. Pat. No. 4,737,593.

Examples include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenyl-phosphine oxide, bis-(2,6-dichlorobenzoyl)-4-biphenylylphosphine oxide, bis-(2,6-dichloro-benzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenyl-phosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxy-benzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenyl-phosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate.

Commercially-available phosphine oxide photo-initiators capable of free-radical initiation when irradiated at wavelengths of greater than 400 nm to 1,200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (formerly known as Irgacure™ 1700, Ciba), 2-benzyl-2-(N,N-dimethylamino)-1-(4-morpholinophenyl)-1-butanone (formerly known as Irgacure™ 369, Ciba), bis($\eta$5-2,4-cyclopentadien-1-yl)-bis(2,6-difluoro-3-(1H-pyrrol-1-yl)phenyl) titanium (formerly known as Irgacure™ 784 DC, Ciba), a 1:1 mixture, by weight, of bis(2,4,6-trimethylbenzoyl)phenyl phosphine oxide and 2-hydroxy-2-methyl-1-phenylpropane-1-one (formerly known as Darocur™ 4265, Ciba), ethyl-2,4,6-trimethylbenzylphenyl phosphine oxide (formerly known as Lucirin™ LR8893X, BASF), and Bis(2,4,6-trimethylbenzoyl)-phenylphosphine oxide (formerly known as Irgacure™ 819, BASF).

Another free-radical initiator system that can alternatively be used includes the class of ionic dye counterion complex initiators comprising a borate anion and a complementary cationic dye.

Borate salt photo initiators are described, for example, in U.S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al), and U.S. Pat. No. 5,057,393 (Shanklin et al.).

Borate anions useful in these photo initiators generally can be of the formula $R^1R^2R^3R^4B^-$, wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetyl-ammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphen-anthroline, 2,4,6-tri(2-pyridyl-s-triazine) and related ligands.

In a further alternative, heat may be used to initiate the hardening, or polymerization, of free radically active groups.

Examples of heat sources suitable for the dental materials of the invention include inductive, convective, and radiant. Thermal sources should be capable of generating temperatures of at least 40° C. to 15° C. under normal conditions or at elevated pressure.

Thermal curing procedures are sometimes preferred for initiating polymerization of materials occurring outside of the oral environment, e.g. when the composition is used for producing mill blanks or in a postcuring step of an article obtained by processing the composition as resin in an additive-manufacturing method.

The initiator system is typically present in the following amounts: at least 0.1, 0.2, or 0.3 wt. %; at most 4, 3, or 2 wt. %; range of 0.1 to 4, 0.2 to 3, or 0.3 to 2 wt. %; wt. % with respect to the whole composition.

The composition described in the present text comprises a filler system. The filler system can comprise one or a mixture of different kinds of fillers.

Adding a filler can be beneficial e.g. for adjusting the rheological properties like viscosity.

The size of the filler particles should be such that a homogeneous mixture with the hardenable component forming the resin matrix can be obtained.

The average particle size of the filler may be in the range from 5 nm to 50 μm. If desired, the measurement of the particle size of the filler particles can be done as described in the example section.

The filler(s) are typically non acid-reactive fillers. A non-acid reactive filler is a filler which does not undergo an acid/base reaction with an acid.

Useful non-acid reactive fillers include fumed silica, fillers based on non-acid reactive fluoroaluminosilicate glasses, quartz, ground glasses, non water-soluble fluorides such as $CaF_2$, silica gels such as silicic acid, in particular pyrogenic silicic acid and granulates thereof, cristobalite, calcium silicate, zirconium silicate, zeolites, including the molecular sieves.

Suitable fumed silicas include for example, products sold under the tradename Aerosil™ series OX-50, -130, -150, and -200, Aerosil™ R8200, R805 available from Evonik, CAB-O-SIL™ M5 available from Cabot Corp (Tuscola), and HDK types e.g. HDK™—H2000, HDK™ H15, HDK™ H18, HDK™ H20 and HDK™ H30 available from Wacker.

Filler(s) which can also be used and which provide radiopacity to the dental materials include heavy metal oxide(s) and fluoride(s). As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling.

Oxides or fluorides of heavy metals having an atomic number greater than 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. yttrium trifluoride and ytterbium trifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are equal or less than 200 nm in average diameter.

Other suitable fillers to increase radiopacity are salts of barium and strontium especially strontium sulphate and barium sulphate.

Filler(s) which can also be used include nano-sized fillers such as nano-sized silica or a mixture of nano-sized silica and zirconia particles. Suitable nano-sized particles typically have an average particle size in the range of 5 to 50 nm.

Preferred nano-sized silicas are commercially available from Nalco Chemical Co. (Naperville, Ill.) under the product designation NALCO™ COLLOIDAL SILICAS (for example, preferred silica particles can be obtained from using NALCO™ products 1040, 1042, 1050, 1060, 2327 and 2329), Nissan Chemical America Company, Houston, Texas (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX™, e.g., P-W50, P-W30, P-X30, P-T40 and P-T40AS); Akzo Nobel Chemicals GmbH, Leverkusen, Germany (for example, those available under the product designation LEVASIL™, e.g., 50/50%, 100/45%, 200/30%, 200A/30%, 200/40%, 200A/40%, 300/30% and 500/15%), and Bayer MaterialScience AG, Leverkusen, Germany (for example, those available under the product designation DISPERCOLL™ S, e.g., 5005, 4510, 4020 and 3030).

Surface-treating the filler particles before loading into the dental material can provide a more stable dispersion in the resin. Preferably, the surface-treatment stabilizes the particles so that the particles will be well dispersed in the resin and results in a substantially homogeneous composition.

Suitable surface treatment or surface modifying agents include silane treatment agents capable of polymerizing with a resin. Preferred silane treatment agent include gamma-methacryloxylpropyltrimethoxysilane, available commercially under the trade designation A-174 (Momentive company) and gamma-glycidoxypropyltrimethoxy silane, a product available under the trade designation G6720 (United Chemical Technologies (Bristol, Pa.)).

Thus, the silica particles as well as other suitable non acid-reactive fillers can be treated with a resin-compatibilizing surface treatment agent.

Suitable filler can also be characterized by the following properties alone or in combination: specific surface (BET): 10 to 400 or 15 to 300 or 20 to 200 m$^2$/g; comprising particles of $SiO_2$, $ZrO_2$ and mixtures thereof, in particular mixtures thereof.

If desired, the specific surface can be determined according to the method suggested by Brunauer, Emmet and Teller (BET) by using a device (Monosorb) available from Quantachrome.

The fillers may comprise, contain, consist essentially or consist of aggregated nano-sized particles. If desired, this can be proven by transmission electron microscopy (TEM).

Once dispersed in the resin, the aggregated nano-sized filler typically remains in an aggregated stage. That is, during the dispersion step the particles do not break up into discrete (i.e. individual) and un-associated (i.e. non-agglomerated, non-aggregated) particles.

Aggregated fillers and processes for the production and surface treatment thereof are described e.g. in U.S. Pat. No. 6,730,156 (Wu et al.) and U.S. Pat. No. 6,730,156 (Windisch et al.).

The amount of filler to be used in the filler system usually depends on the purpose for which the composition should be used.

The filler system is typically present in the following amounts: at least 20, 30, or 40 wt. %; at most: 90, 85, or 80 wt. %; range of 20 to 90, 30 to 85, or 40 to 80 wt. %; wt. % with respect to the whole composition.

Depending on the use, the amount of the filler system is typically adjusted.

Temporary crown and bridge materials (as an example for a dental composition) usually do not contain a high amount of fillers. With respect to these compositions, the filler content usually is in a range of 30 to 60 wt. % with respect to the whole composition.

In dental filling materials (as an example of a dental composition; sometimes also referred to as dental composite materials), which typically contain a higher amount of fillers compared to temporary crown and bridge materials, the filler content is usually in a range of 60 to 90 wt. % with respect to the whole composition.

Lower viscous dental filling materials (sometimes also referred to as "flowables") typically have a filler content in the range of 50 to 80 wt. % with respect to the whole composition.

The composition described in the present text can comprise additional components.

Additional components which can be present include plasticisers and adjuvants.

Plasticisers may comprise hydroxyl groups, but typically no polymerizable moieties.

If present, the hydroxyl group containing plasticiser may contain two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32 g/mol) to very high (e.g., one million or more g/mol). Suitable hydroxyl-containing materials can have low molecular weights, i.e. from 32 to 200 g/mol, intermediate molecular weight, i.e. from 200 to 10,000 g/mol, or high molecular weight, i.e. above 10,000 g/mol. As used herein, all molecular weights are weight average molecular weights.

The hydroxyl group containing plasticiser can be non-aromatic in nature or can contain aromatic functionality. The hydroxy group containing plasticiser can optionally contain heteroatoms in the backbone of the molecule, such as nitrogen, oxygen, sulfur, and the like. The plasticiser can, for example, be selected from naturally occurring or synthetically prepared cellulosic materials.

Representative examples of a suitable hydroxy group containing plasticiser include alkanols, monoalkyl ethers of polyoxyalkyleneglycols, monoalkyl ethers of alkylene-glycols, and others known in the art.

Representative examples of useful plasticisers include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; and castor oil.

Representative examples of useful polymeric hydroxy group containing plasticisers include polyoxyethylene and polyoxypropylene glycols, and particularly the polyoxyethylene and polyoxy-propylene glycol diols and triols having molecular weights from 200 to 10,000 g/mol corresponding to a hydroxy equivalent weight of 100 to 5,000 for the diols or 70 to 3,300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Blends of various hydroxy group containing plasticisers are also contemplated in the present text.

The plasticiser is typically present in the following amounts: 0 or at least 1 or 5 wt. %; at most 20, 15 or 10 wt. %; range from 0 to 20, 1 to 15, or 5 to 10 wt. %; wt. % with respect to the weight of the whole composition.

The compositions can also contain suitable adjuvants or additives such as surfactants, rheology modifiers, retarders, stabilizers, pigments, dyes, photo bleachable colorants, fluoride release agents and other ingredients well known to those skilled in the art.

Surfactants which can be added include polyethylene glycol modified siloxanes (e.g. Silwet™ type surfactants available from Momentive) and polyethylene glycol modified carbosilanes (described e.g. in U.S. Pat. No. 5,750,589 (Zech et al.).

Rheology modifiers which can be added include surface modified fumed silica as described above, organophilic phyllosilicates, modified ureas and polyhydroxycarboxylic acid amides (e.g. Rheobyk™ types available from Byk-Chemie, Wesel, Germany).

Retarders which can be added include 1,2-diphenyl ethylene, and derivatives thereof.

Stabilizers which can be used include especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydro-quinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentyl-phenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers).

Pigments and/or dyes which can be used include titanium dioxide or zinc sulphide (lithopones), red iron oxide 3395, Bayferrox™ 920 Z Yellow, Neazopon™ Blue 807 (copper phthalocyanine-based dye) or Helio™ Fast Yellow ER. These additives may be used for individual coloring of the compositions.

Examples of photo bleachable colorants include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photo bleachable colorants can be found in U.S. Pat. No. 6,444,725 (Trom et al.).

Examples of fluoride release agents include naturally occurring or synthetic fluoride minerals. These fluoride sources can optionally be treated with surface treatment agents.

Adjuvants are typically present in the following amounts: at least 0, 0.01, or 0.1 wt. %; at most 15, 10 or 5 wt. %; range from 0 to 15, or 0.01 to 10, or 0.1 to 5 wt. %; wt. % with respect to the weight of the whole composition.

The composition described in the present text may comprise the respective components in the following amounts:
 a) polymerizable component A1: 3 to 50 wt. %,
 b) polymerizable component A2: 0 to 60 wt. %,
 c) initiator system: 0.1 to 4 wt. %,
 d) filler system: 20 to 90 wt. %,
 e) plasticiser: 0 to 20 wt. %,
 f) adjuvants: 0 to 15 wt. %,
wt. % with respect to the weight of the whole dental composition.

The composition described in the present text may also comprise the respective components in the following amounts:
 a) polymerizable component A1: 5 to 40 wt. %,
 b) polymerizable component A2: 1 to 50 wt. %,
 c) initiator system: 0.2 to 3 wt. %,
 d) filler system: 30 to 85 wt. %,
 e) plasticiser: 1 to 15 wt. %,
 f) adjuvants: 0.01 to 10 wt. %,
wt. % with respect to the weight of the whole dental composition.

The composition described in the present text may also comprise the respective components in the following amounts:
 a) polymerizable component A1: 8 to 30 wt. %,
 b) polymerizable component A2: 5 to 40 wt. %,
 c) initiator system: 0.3 to 2 wt. %,
 d) filler system: 40 to 80 wt. %,
 e) plasticiser: 5 to 10 w. %,
 f) adjuvants: 0.1 to 5 wt. %,
wt. % with respect to the weight of the whole dental composition.

Certain embodiments of the composition can be further characterized by the following physical-mechanical properties after hardening alone or in combination:
 a) flexural strength (FS): 140 to 200 MPa*s determined according to ISO 4049 (2019);
 b) E-Modulus (E-M): 4 to 16 GPa determined according to ISO 4049 (2019);
 c) depth of cure (DoC): 3 to 7 mm determined according to ISO 4049 (2019);
 d) bonded Disk Shrinkage-Strain (SHR): 1.50 to 1.80%;
 e) diametral Tensile Strength (DTS): 75 to 100 determined according to ISO 7489 (2019);
 f) Cusp deflection (Cusp-D): <12 µm.

Certain embodiments of the composition are characterized by the following physical-mechanical properties after hardening alone or in combination:
 a) Flexural strength (FS): 150 to 200 MPa*s determined according to ISO 4049 (2019);
 b) E-Modulus (E-M): 4 to 10 or 12 to 16 GPa determined according to ISO 4049 (2019);
 c) Depth of cure (DoC): 4 to 6 mm determined according to ISO 4049 (2019);
 d) Bonded Disk Shrinkage-Strain (SHR): 1.55 to 1.75%;
 e) Diametral Tensile Strength (DTS): 80 to 100 determined according to ISO 7489 (2019);
 a) Cusp deflection (Cusp-D): 8 to 11.

A combination of the following physical-mechanical properties is sometimes preferred: a) and b); a) and c); a), b) and c); a), c) and f; a), c) and d).

Certain embodiments of the composition can be further characterized by the following physical-mechanical properties before hardening alone or in combination:
 a) Viscosity: 5 to 100 Pa*s at 23° C. and a shear rate of 100 s−1.
 b) pH-value: 6 to 8;
 c) hardenable within 10 min after irradiation with light having a wavelength in the range of 400 to 700 nm.

For flowable composite materials, a combination of the following physical-mechanical properties is sometimes preferred: a) and b) or a) and c).

A low viscosity can be advantageous as it allows the composition to flow also in deep cavities of a prepared tooth structure which otherwise might be difficult to fill.

As the composition does typically not contain acidic substances, the pH-value is essentially in the neutral range.

All components used in the composition described in the present text should be sufficiently biocompatible, that is, the composition should not produce a toxic, injurious, or immunological response in living tissue.

The composition described in the present text does typically not contain the following components alone or in combination: low boiling solvents (e.g. boiling point below 150° C. at ambient pressure) in an amount of 5 wt. % or more; Bis-GMA or a bis-phenol A moiety derived component in an amount of 2 wt. % or more; polymerizable components comprising an acidic moiety in an amount of 2 wt. % or more.

The composition described in the present text can be obtained by combining (including mixing and kneading) the individual components of the composition, preferably under "safe light" conditions. If desired, a speed-mixer can be used.

The composition obtained can be hardened in an acceptable time frame, e.g., less than 10 min or less than 5 min or less than 2 min, and to a sufficient depth using visible light source equipment already available to the practitioner.

Further embodiments of the invention include:

Embodiment 1

The composition may comprise, consist essentially of, or consist of the following components:

a) polymerizable component A1 in an amount of 3 to 50 wt. %,
b) polymerizable component A2 in an amount of 0 to 60 wt. %,
c) initiator system in an amount of 0.1 to 4 wt. %, the initiator system comprising a ketone sensitizer and an amine donor,
d) filler system comprising nano-sized particles in an amount of 20 to 90 wt. %,
e) plasticiser in an amount of 0 to 20 wt. %,
f) adjuvants in an amount of 0 to 15 wt. %,
the composition not comprising a bis-phenol A moiety containing component in an amount of 5 wt. % or more, wt. % with respect to the weight of the whole composition.

Embodiment 2

The composition may comprise, consist essentially of, or consist of the following components:
a) polymerizable component A1 in an amount of 5 to 40 wt. %,
b) polymerizable component A2 being characterized by the following formula:

$A_n BA_m$ with A being an ethylenically unsaturated group,
B being selected from (i) linear or branched $C_1$ to $C_{12}$ alkyl, optionally substituted with halogenides, or OH (ii) $C_6$ to $C_{12}$ aryl, optionally substituted with halogenides or OH, or (iii) organic group having 4 to 20 carbon atoms bonded to one another by one or more ether, thioether, ester, thioester, thiocarbonyl, amide, urethane, carbonyl and/or sulfonyl linkages,
m, n being independently selected from 0, 1, 2, 3, 4, 5 or 6 with the proviso that n+m is greater 0. and in an amount of 1 to 50 wt. %,
c) initiator system in an amount of 0.1 to 4 wt. %, the initiator system comprising a ketone sensitizer and an amine donor,
d) filler system comprising nano-sized silica particles in an amount of 20 to 90 wt. %,
e) plasticiser in an amount of 0 to 20 wt. %,
f) adjuvants in an amount of 0 to 15 wt. %,
the composition not comprising bis-phenol A containing components in an amount of 5 wt. % or more,
wt. % with respect to the weight of the whole composition.

Embodiment 3

The composition described in the present text may comprise, consist essentially of, or consist of
a) polymerizable component A1 in an amount of 3 to 50 wt. %,
b) polymerizable component A2 in an amount of 5 to 60 wt. %,
c) initiator system in an amount of 0.1 to 4 wt. %, the initiator system comprising a ketone sensitizer and an amine donor,
d) filler system comprising nano-sized particles, in an amount of 60 to 90 wt. %,
e) plasticiser in an amount of 0 to 20 wt. %,
f) adjuvants in an amount of 0 to 15 wt. %,
wt. % with respect to the weight of the whole composition.

Embodiment 4

The composition described in the present text may comprise, consist essentially of, or consist of
a) polymerizable component A1 in an amount of 3 to 50 wt. %,
b) polymerizable component A2 in an amount of 0 to 60 wt. %,
c) initiator system in an amount of 0.1 to 4 wt. %, the initiator system comprising a ketone sensitizer and an amine donor,
d) filler system comprising nano-sized particles in an amount of 50 to 80 wt. %,
e) plasticiser in an amount of 0 to 20 wt. %,
f) adjuvants in an amount of 0 to 15 wt. %,
wt. % with respect to the weight of the whole composition, the composition having a viscosity of 5 to 100 Pa*s at 23° C. and 100 s$^{-1}$.

The composition is typically provided to the practitioner under hygienic conditions. During storage, the composition is typically packaged in a suitable packaging and/or delivery device.

One possibility to achieve this includes packing or storing the composition in a sealed container.

A suitable container may have a front end and a rear end, a piston movable in the container and a nozzle or cannula for delivering or dispensing the composition located in the container. The container has usually only one compartment or reservoir.

The volume of the container is typically in the range of 0.1 to 100 ml or 0.5 to 50 ml or 1 to 30 ml.

A suitable single-use container may have a volume in the range of 0.1 to 2 ml. This is the volume typically needed for a single application procedure. Such a container is typically used only once (e.g. disposable packing).

The composition can be dispensed out of the container by moving the piston in the direction of the nozzle. The piston can be moved either manually or with the aid of an application device or applier designed to receive the container (e.g. an application device having the design of a caulk gun).

Examples of containers which can be used include compules, syringes and screw tubes.

The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun).

Examples of suitable compules or containers are described in U.S. Pat. No. 5,624,260 (Wilcox et al.), EP 1 340 472 A1 (Centrix), US 2007/0172789 A1 (Mueller et al.), and U.S. Pat. No. 5,865,803 (Major). Further suitable containers are exemplified in U.S. Pat. No. 5,927,562 (Hammen et al) and US 2011/151403 A1 (Pauser et al.).

It can be advantageous, if a container is used comprising a nozzle having a shape and size, which allows an easy and safe application of the composition to the soft dental tissue surrounding the tooth to be restored, also near the interdental region.

The smaller the diameter of the nozzle is, the easier the nozzle can be placed into the region between two teeth. However, a small diameter of the nozzle may result in an increase of the extrusion force needed for dispensing the composition out of the device. Thus, not all cannula sizes and diameters are equally suitable. A device with a nozzle or cannula having an external diameter in the range from 0.6 mm to 1.3 mm and an internal diameter in the range from 0.2 mm to 0.9 mm has been found to be particular useful.

Another embodiment of the invention is directed to a kit of parts comprising at least two, three, four, five, six or more compositions which differ from each other at least with respect to their colour. As outlined above, the compositions are typically stored in a container.

The composition described in the present text is in particular useful in the dental and orthodontic field.

The composition can be used as or for producing a dental restoration. Dental restorations are typically produced outside the mouth of a patient and inserted later in a treatment step.

Examples of dental restorations include direct restorative materials (e.g., anterior and posterior restoratives), prostheses, veneers, artificial crowns, artificial teeth, dentures, and the like.

The term "prosthesis" as used herein refers to a composite that is shaped and polymerized for its final use (e.g., as a crown, bridge, veneer, inlay, onlay or the like) before it is disposed adjacent to a tooth.

When the dental material is applied to a tooth, the tooth can optionally be pre-treated with a primer such as dentin or enamel adhesive by methods known to those skilled in the art.

More precisely, the composition can be used for the treatment of hard dental tissue in the mouth of a mammal, in particular a human being.

Such a treatment method typically comprises the following steps:
  a) placing the composition described in the present text in contact with the surface of hard dental tissue,
  b) hardening the composition.

More particularly, the process may comprise the steps of
  c) applying the dental composition to the surface of hard dental tissue; if desired, the surface of the hard dental tissue can be an etched surface (e.g. with phosphoric acid) or a non-etched surface,
  d) optionally dispersing the dental composition to a thin film, preferably using a stream of air,
  e) radiation curing of the dental composition.

In particular, the composition may be used as composite fillings material, cavity liner, fixing material for orthodontic appliances or sealant.

The term "composite filling material" refers to a filled dental composition. A dental composite material is typically used for restoring a defect tooth structure in the mouth of a patient.

A "cavity liner" means a composition for protecting the pulp before a composite filling material or dental restoration is applied.

The term "sealant" as used herein refers to a lightly filled dental composite material that is cured after it is disposed adjacent to a tooth. Sealants are typically applied to the back teeth and form a protective shield over the enamel of the tooth.

In a preferred aspect, the dental material is a low-viscous dental filling material.

In a further embodiment the dental composition described in the present text is used for producing a dental mill blank.

A dental mill blank can be produced by placing the curable composition into a mould followed by a curing step.

In another embodiment the dental composition is used as resin in an additive-manufacturing method for producing a 3-dimensional object (such as a dental article) layer-by-layer, e.g. by applying a 3d-printing technique.

The invention also relates to a kit of parts comprising the composition described in the present text and the following items alone or in combination: dental adhesive; dental primer; dispensing device; polishing equipment; dental curing light; optionally instruction for use.

Dental adhesives are typically acidic dental composition with a rather low viscosity (e.g. 0.01 to 3 Pa*s at 23° C.). Dental adhesives directly interact with the enamel or dentin surface of a tooth. Dental adhesives are typically one-part compositions, are radiation-curable and comprise ethylenically unsaturated component(s) with acidic moiety, ethylenically unsaturated component(s) without acidic moiety, water, sensitizing agent(s), reducing agent(s) and additive(s).

Examples of dental adhesives are described in US 2020/0069532 A1 (Thalacker et al.) and US 2017/0065495 A1 (Eckert et al.). Dental adhesives are also commercially available, e.g. 3M™ Scotchbond™ Universal (3M Oral Care).

Suitable dental primers are described in U.S. Pat. No. 6,126,922 (Rozzi et al.) and WO 00/69393 A1 (3M). Dental primers are also commercially available, e.g. 3M™ Transbond™ XT Primer (3M Oral Care).

Suitable polishing equipment include rubber cuss, polishing paste, and polishing discs. Polishing devices are also commercially available, e.g. Soflex™ discs (3M Oral Care).

Suitable dental curing lights are described in U.S. Pat. No. 10,758,126 B2 (Geldmacher et al.) or U.S. Pat. No. 10,231,810 B2 (Gramann et al). Dental curing lights are also commercially available, e.g. 3M™ Elipar™ S10 or 3M™ Elipar™ DeepCure S LED curing light (3M Oral Care).

A suitable dispensing device is described in US 2021/113301 A1 (Pauser et al.). Dispensing devices are also commercially available, e.g. 3M™ Capsule Dispenser (3M Oral Care).

The instruction for use describes how the dental composition should be used in daily practice, e.g. outlining the application steps and curing conditions.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

Examples

Unless otherwise indicated, all parts and percentages are on a weight basis, all water is deionized water, and all molecular weights are weight average molecular weight (g/mol). Moreover, unless otherwise indicated all experiments were conducted at ambient conditions (23° C.; 1013 mbar). Moreover, nearly all process steps were conducted under an atmosphere of dry air.

Methods pH Value

If desired, the pH value of a composition can be determined as follows: A pH sensitive paper (Carl Roth™ company) is provided. A stripe of the pH sensitive paper is wetted. A small portion of the composition to be tested is placed on the wetted pH sensitive paper. After 5 s the colour change of the pH sensitive paper is determined.

Particle Size Distribution (Non Nano-Sized Particles)

If desired, the particle size distribution can be determined by light-scattering, e.g. using the device Horiba (Horiba, JP).

The light scattering particle-sizer illuminates the sample with a laser and analyzes the intensity fluctuations of the light scattered from the particles at an angle of 173 degrees. The method of Photon Correlation Spectroscopy (PCS) can be used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size. In the scope of this document the Z-average size is referred to as "average particle size".

Particle Size Distribution (Nano-Sized Particles)

The measurement of the size of nano-particles is preferably based on a TEM (transmission electron microscopy) method, whereby a population is analyzed to obtain an average particle diameter. A preferred method for measuring the particle diameter can be described as follows:

Samples approximately 80 nm thick are placed on 200 mesh copper grids with carbon stabilized formvar substrates (SPI Supplies—a division of Structure Probe, Inc., West Chester, PA). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

Flexural Strength (FS)

If desired, the measurement of the flexural strength can be carried out according to ISO 4049 (2019) using a universal testing machine (Zwick Z 010, crosshead speed 1 mm/min). The flexural strength is typically given in MPa.

E-Modulus (EM)

If desired, the EM can be determined according to ISO 4049 (2019) and is given in [GPa].

Bonded Disk Shrinkage-Strain (SHR)

If desired, the Bonded Disk Shrinkage-Strain can be determined according to the Watts protocol as described in more detail in Dent. Mater. 1991, 7, 281-287. Unit: [%].

Depth of Cure (DoC)

Depth of cure (i.e., cure depth) was analyzed according to ISO 4049 (2019) by packing a paste sample into a cylindrical metal curing mould (8 mm deep, 4 mm diameter) and curing the sample for 40 s with an Elipar™ Trilight Standard (800 mW/cm$^2$) (3M Oral Care). The cured sample was removed from the mould and uncured paste was scraped off of the sample with a plastic applicator after less than about one minute of curing. Results were reported as the average of three replicates.

Refractive Index ($n_D^{20}$)

If desired, the refractive index can be measured with a Kruess AR 4 D device (refractometer according to Abbe's measure principle). The refractive index is typically measured at 20.0° C. at a wavelength of 589 nm.

Viscosity ($\eta$)

If desired, the viscosity can be measured with a Physica MCR 301 (Anton Paar Germany GmbH, Ostfildern-Scharnhausen). Monomers are tested at 23.0° C. with a shear rate of 100/s using a 25 mm/1° cone/plate system. Flowable composites can be measured at 25.0° C. with a shear rate of 100/s with a 15 mm plate/plate system and a gap of 0.2 mm.

Cusp Deflection (Cusp-D)

If desired, the cusp deflection can be measured according to the following method:

A slot is machined into a rectangular 15×10×8 mm aluminum block. The slot is 8 mm long, 4.0 mm deep and 4.0 mm across, and is located 2 mm from an edge, thus forming a 4 mm wide aluminum cusp adjacent to a 4 mm wide cavity containing dental compositions being tested. A linear variable displacement transducer (MODEL GT 1000, used with an E309 analog amplifier, both from RDP Electronics, UK) is positioned to measure the displacement of the cusp tip as the dental composition photocured at room temperature. Prior to testing, the slot in the aluminum block is sandblasted using Rocatec™ Plus Special Surface Containing Blasting Material (3M Oral Care), treated with RelyX™ Ceramic Primer (3M Oral Care), and finally treated with a dental adhesive, Scotchbond™ Universal (3M Oral Care).

The slot is fully packed with a paste sample, which equaled approximately 250 mg of material. The material was irradiated for 1 min with a dental curing lamp (Elipar™ S10, 3M Oral Care) positioned close (about 2 mm) with the material in the slot, then the displacement of the cusp in micrometers is recorded 9 min after the lamp was extinguished.

Diametral Tensile Strength (DTS)

If desired, the DTS can be measured according to the following method:

A paste sample is injected into a 4-mm (inside diameter) glass tube; the tube is capped with silicone rubber plugs; and then the tube is compressed axially at approximately 2.88 kg/cm$^2$ pressure for 5 min. The sample is then light cured for 4*20 s by exposure to a Elipar™ DeepCure dental curing light (3M Oral Care)

Cured samples are then cut with a diamond saw to form 2.5 mm long cylindrical plugs for measurement of compressive strength. The plugs are stored in de-ionized water at 36° C. for about 24 hs prior to testing. Measurements are carried out on a Zwick/Roell Universal tester (Zwick/Roell GmbH & Co. KG, Ulm, Germany) with a 10 kilonewton (kN) load cell at a crosshead speed of 1 mm/min according to ANSI/ADA Specification 27.

Compositions

Abbreviations

The name and/or structure of the components used are given in Table 1.

TABLE 1

| | | |
|---|---|---|
| AA | Acrylic acid (CAS no. 79-10-7) | |
| BC | 4-tert-Butylcatechol (CAS no. 98-29-3) | |
| BCGP | 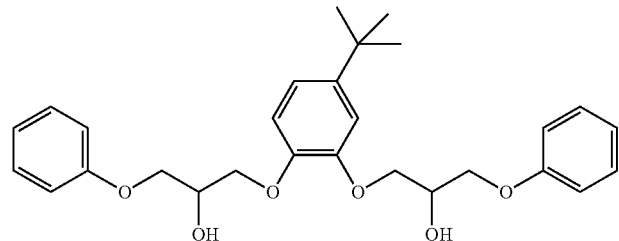 [SMILES: CC(C)(C)c1ccc(OCC(O)COc2ccccc2)c(OCC(O)COc2ccccc2)c1]<br>Mw = 466.6 | |
| BCGPaEO | 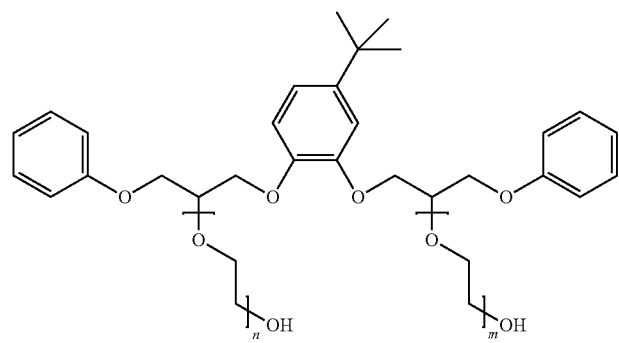<br>(m + n) = 1 to 10 | |
| BCGP2.5EO-DMA | 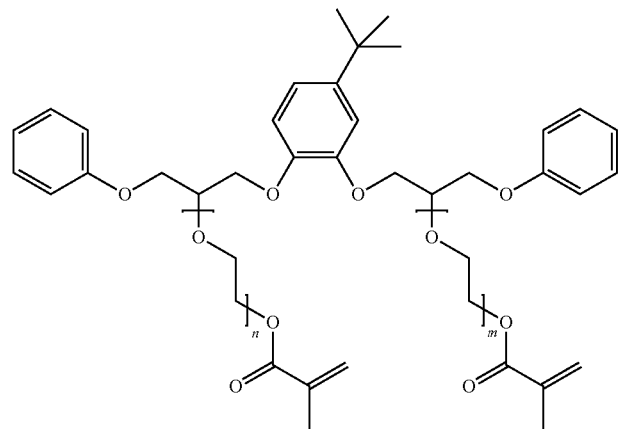<br>(m + n) = 2.5, Mw = 727.41; $n_D^{20}$ = 1.535; $\eta$ = 5.3 Pa*s | IE5   f) |
| BHT | 2,6-Di-tert-butyl-4-methylphenol (CAS no. 7637-07-2) | |
| CPQ | Camphorquinone (CAS no. 10373-78-1) | f) |
| DPI-PF6 | Diphenyliodonium hexafluorophosphate (CAS no. 58109-40-3) | g) |
| EC | Ethylene carbonate (CAS no. 96-49-1) | |
| EDMAB | Ethyl 4-dimethylaminobenzoate (CAS no. 10287-53-3) | h) |
| EO | Ethylene oxide (CAS no. 75-21-8) | |
| ER | 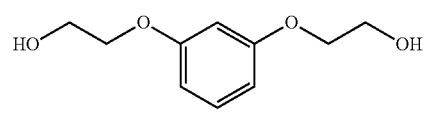 [SMILES: OCCOc1cccc(OCCO)c1]<br>Ethoxylated resorcinol (CAS no. 102-40-9) | |

TABLE 1-continued

ERGP
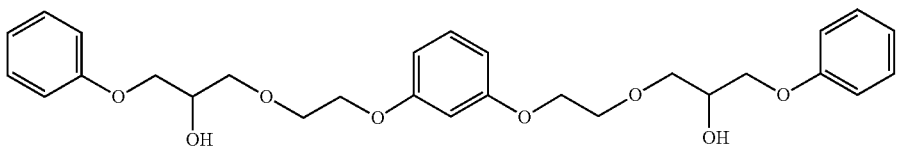 [SMILES: OC(COCCOc1cccc(OCCOCC(O)COc2ccccc2)c1)COc1ccccc1]
Mw = 498.6

ERGP-MA    CE1   a)
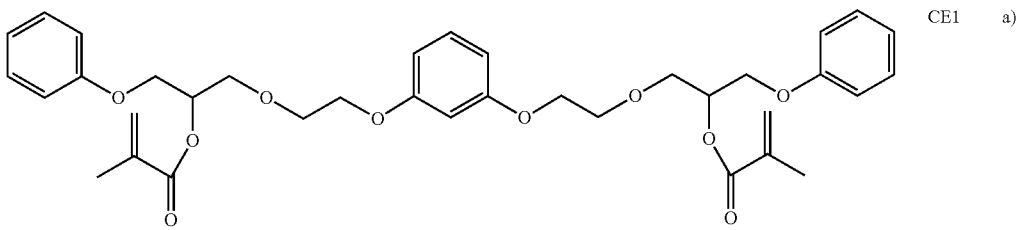
Mw = 634.7; $n_D^{20}$ = 1.542; η = 9.4 Pa*s

ERGP-A    CE2
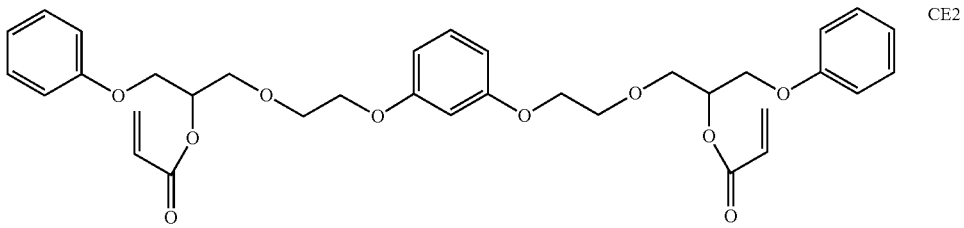
Mw = 606.7; $n_D^{20}$ = 1.547; η = 18.8 Pa*s

| | |
|---|---|
| Filler | Spray dried zirconia silica filler, <1 μm, surface treated; cf. example 1 of U.S. Pat. No. 4,503,169 (Randklev et al) silanized according to U.S. Pat. No. 6,030,606 (Holmes et al.)    j) |
| GP | Glycidyl phenyl ether (CAS no. 122-60-1) |
| HQ | Hydroquinone (CAS no. 75-21-8) |
| HQME | Hydroquinone methyl ester (CAS no. 150-76-5) |
| KOH | Potassium hydroxide (CAS no. 1310-58-3) |
| KOtBu | Potassium tert-butoxide (CAS no. 865-47-4) |
| MA | Methacrylic acid (CAS no. 79-41-4) |
| MSA | Methane sulfonic acid, 70% (CAS no. 75-75-2) |
| NaOH | Sodium hydroxide (CAS no. 1310-73-2) |
| Phlo | Phloroglucinol (CAS no. 108-73-6) |

PhloGP
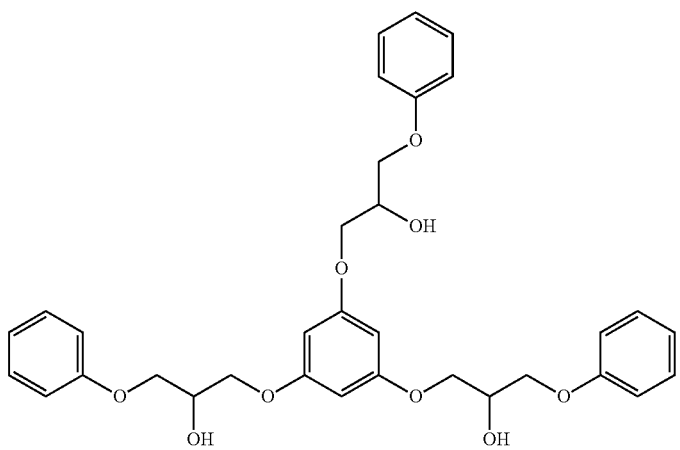 [SMILES: OC(COc1ccccc1)COc1cc(OCC(O)COc2ccccc2)cc(OCC(O)COc2ccccc2)c1]
Mw = 576.7

TABLE 1-continued
PhloGPbEO
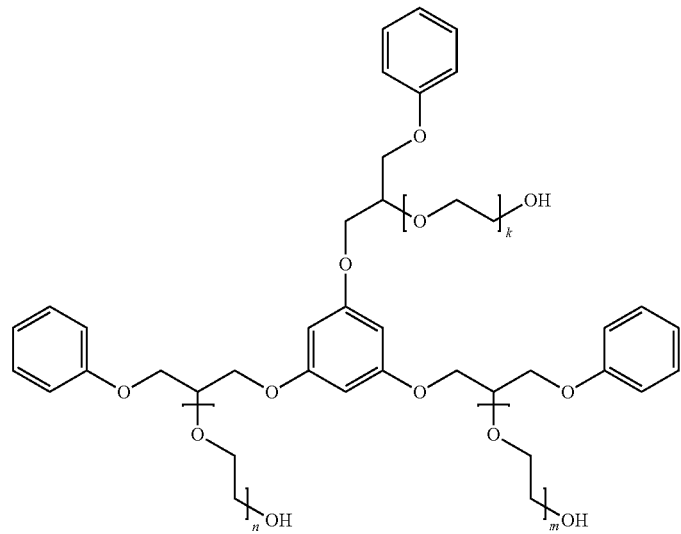
(k + m + n) = 1 to 15
PhloGP6EO-
TMA
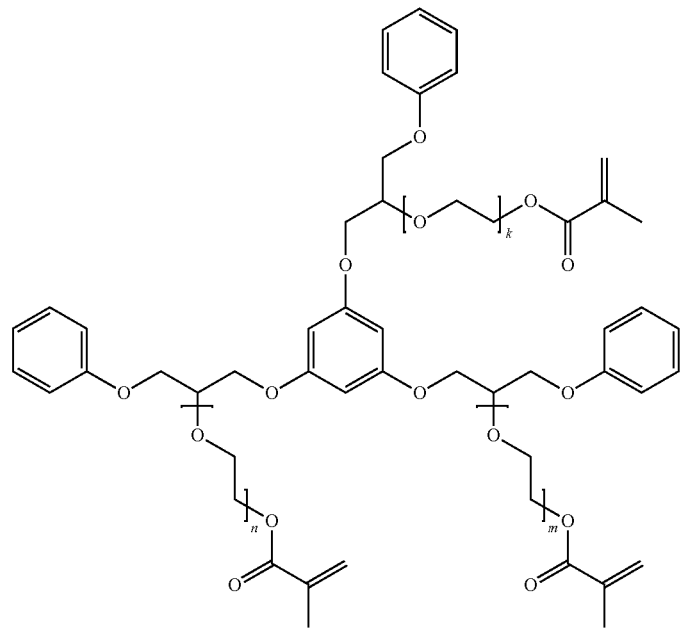
IE6
(k + m + n) = 6; Mw = 1045.2; $n_D^{20}$ = 1.538; $\eta$ = 14.6 Pa*s TABLE 1-continued
| | | |
|---|---|---|
| PhloGP6EO-TA | 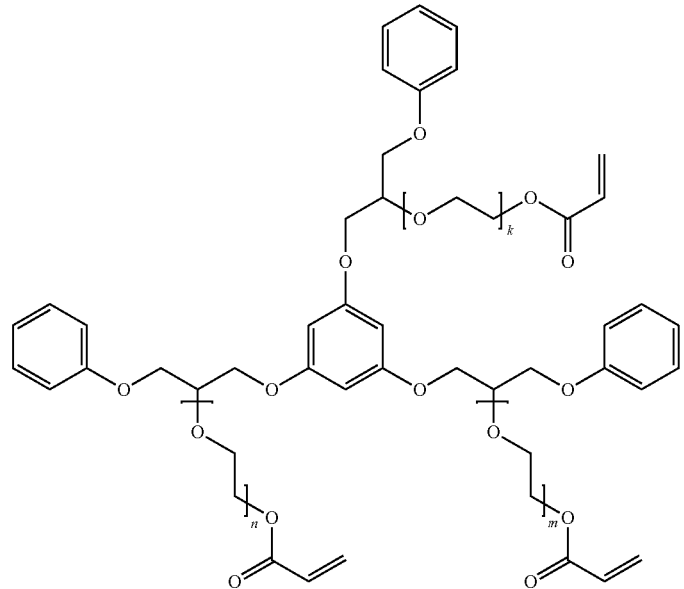 $(k + m + n) = 6$; Mw = 1003.1; $n_D^{20}$ = 1.543; $\eta$ = 30.3 Pa*s | IE7 |
| PO | Propylene oxide (CAS no. 75-56-9) | |
| PTZ | Phenothiazine (CAS no. 92-84-2) | |
| R | Resorcinol (CAS no. 108-46-3) | |
| RGP | 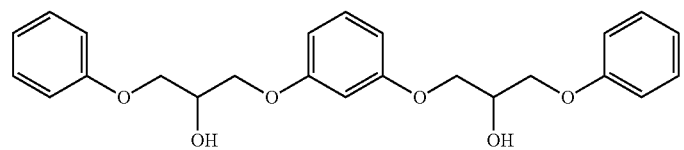 Mw = 410.5 | |
| RGPaEO | 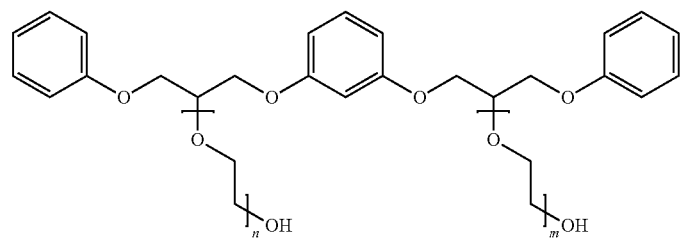 $(m + n) = 1$ to 10 | |
| RGP2.2EO-DMA | 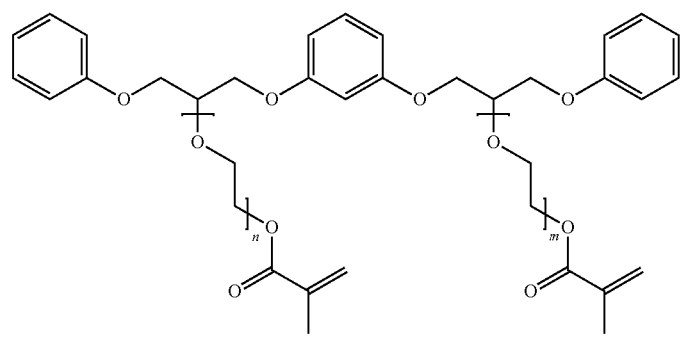 $(m + n) = 2.2$; Mw = 634.7; $n_D^{20}$ = 1.542; $\eta$ = 5.5 Pa*s | IE1 b) |

TABLE 1-continued

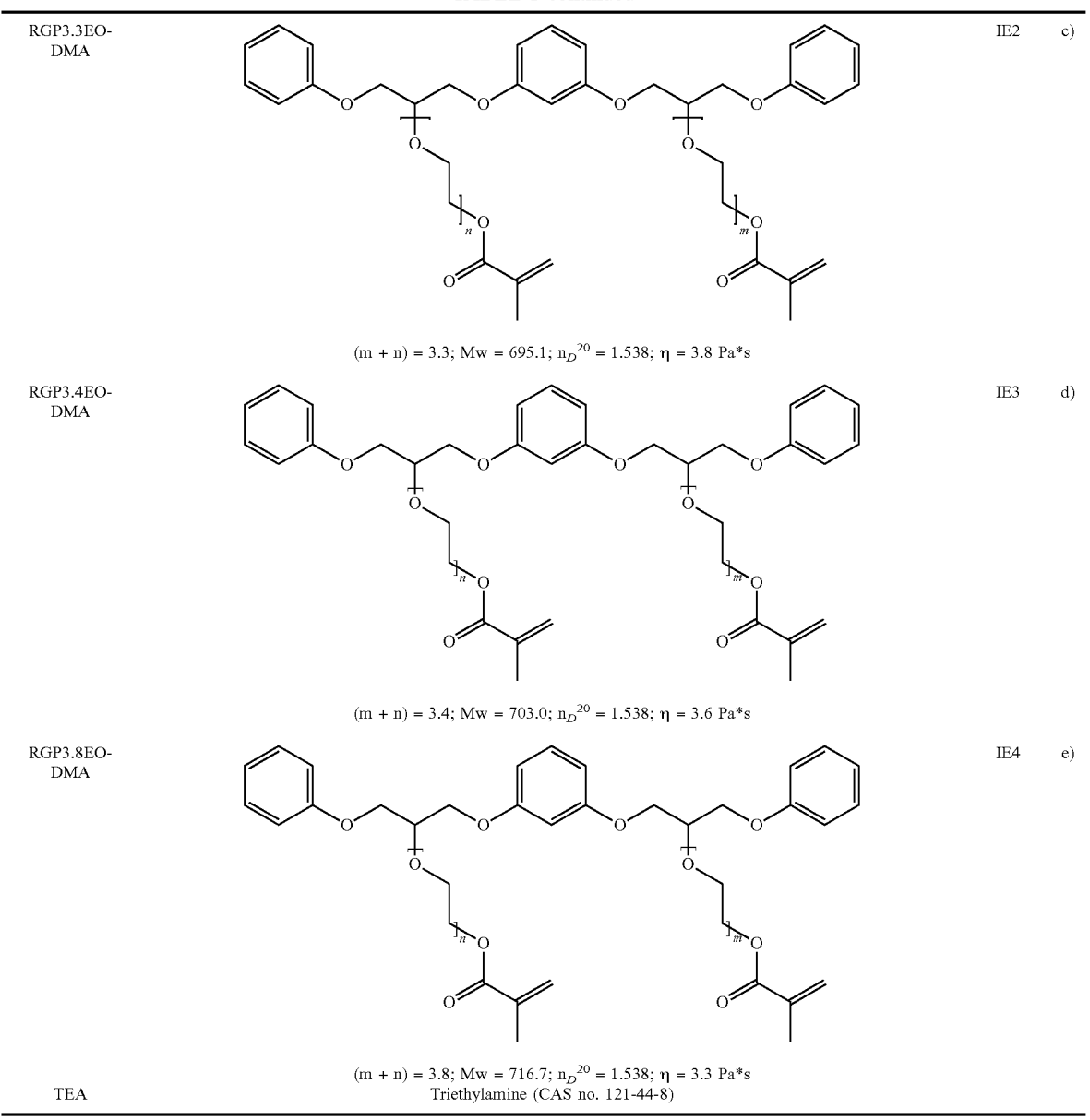

| | | |
|---|---|---|
| RGP3.3EO-DMA | (m + n) = 3.3; Mw = 695.1; $n_D^{20}$ = 1.538; η = 3.8 Pa*s | IE2 c) |
| RGP3.4EO-DMA | (m + n) = 3.4; Mw = 703.0; $n_D^{20}$ = 1.538; η = 3.6 Pa*s | IE3 d) |
| RGP3.8EO-DMA | (m + n) = 3.8; Mw = 716.7; $n_D^{20}$ = 1.538; η = 3.3 Pa*s | IE4 e) |
| TEA | Triethylamine (CAS no. 121-44-8) | |

CE stands for comparative example, IE stands for inventive example.

Synthesis Compound (A)

Compound(s) (A) can be prepared as follows:

General Procedure 1: Synthesis of Alkoxylated Intermediates Using e.g. Ethylene Carbonate (EC)

Under a protective $N_2$ atmosphere the phenolic compound (e.g. resorcinol) and glycidyl phenyl ether (1 eq. per phenolic OH group) and a basic catalyst (e.g. KOH or NaOH or KOtBu, at least 3 mol-% with respect to 1 phenolic OH group) are stirred at a temperature of at least 100° C. until the epoxy groups have reacted completely (detection via $^1$H NMR in $CD_3OD$). Then ethylene carbonate is added (at least 1 ethylene carbonate per 1 initial phenolic OH group) and the mixture is stirred at a temperature of at least 140° C. until ethylene carbonate has reacted completely (detection via $^1$H NMR in $CD_3OD$). Both reaction steps can either be done subsequently as one pot reaction or separately as two separate reactions. The synthesis of the alkoxylated intermediate can be done as classical batch reaction (pressureless or pressurized) or continuously under pressure using a flow reactor.

Then the reaction mixture is cooled to about 80° C. and 130 wt. % of 2N NaOH solution (with respect to the theoretical yield) are added. This mixture is heated to reflux for at least 2 h so that the carbonates within the EO side chains are hydrolysed (detection via $^1$H NMR in $CD_3OD$). The mixture is cooled to RT and diluted with 200 wt. % of toluene or ethyl acetate (with respect to the theoretical yield). The organic phase is separated and extracted several times with water. Then 10 wt. % of $Na_2CO_3$ and 10 wt. % of charcoal (each with respect to the theoretical yield) are added to the organic phase and this mixture is stirred overnight under air. After filtration from $Na_2CO_3$/charcoal the filtrate is filtered again through 20 wt. % of neutral alumina (with respect to the theoretical yield) and the solvent is stripped off from the filtrate in vacuo. The yields of the ethoxylated intermediates are about 90%.

General Procedure 2: Esterification of Alkoxylated Intermediates with e.g. Methacrylic Acid (MA)

To the ethoxylated intermediates in e.g. hexane and/or cyclohexane and/or toluene BHT and/or HQME, optionally methylene blue and/or PTZ, e.g. methane sulfonic acid or $H_2SO_4$ as catalyst and e.g. methacrylic acid are added. At reflux water is removed using a Dean Starck apparatus. After completion of the reaction the crude reaction mixture is extracted at least twice with aqueous NaOH solution (4N or 2N), then at least once washed with water, optionally dried over anhydrous $Na_2SO_4$. After filtration, the filtrate is again filtered through neutral alumina. At least 100 ppm of BHT and 100 ppm of HQME are added to the filtrate. Then the solvent is stripped off in vacuum while air is bubbling through the crude sample. The yields of the final monomers are about 90%.

Synthesis of ERGP-MA (Comparative Example 1):

ERGP-MA was synthesized according to WO 2012/106083 A1 (3M), page 45.

Synthesis of ERGP-A (Comparative Example 2):

ERGP-A was synthesized according to WO 2012/106083 A1 (3M), page 45.

Synthesis of RGP2.2EO-DMA (Inventive Example 1):

According to General Procedure 1 25.0 g of R, 68.6 g of GP, and 79.9 g of EC were reacted using KOtBu as catalyst. 112 g of RGP2.2EO (225 mmol, 98.9%) were isolated as yellowish liquid. According to General Procedure 2 49.9 g of RGP2.2EO, 25.8 g of MA, 94.7 mg of HQME, 3.80 mg of PTZ, and 2.30 g of MSA were reacted using cyclohexane:toluene=92.5:7.50 as solvent. 58.5 g of RGP2.2EO-DMA (92.2 mmol, 92.2%) were isolated as yellowish oil: η=5.5 Pa*s, $n_D^{20}$=1.542.

Synthesis of RGP3.3EO-DMA (Inventive Example 2):

According to General Procedure 1 60.0 g of R, 165 g of GP, and 288 g of EC were reacted using KOH as catalyst. 290 g of RGP3.3EO (494 mmol, 90.7%) were isolated as yellowish liquid. According to General Procedure 2 96.0 g of RGP3.3EO, 43.7 g of MA, 175 mg of HQME, 7.00 mg of PTZ, and 4.20 g of MSA were reacted using cyclohexane:toluene=70.0:30.0 as solvent. 109 g of RGP3.3EO-DMA (140 mmol, 91.0%) were isolated as yellowish oil: η=3.8 Pa*s, $n_D^{20}$=1.538.

Synthesis of RGP3.4EO-DMA (Inventive Example 3):

According to General Procedure 1 25.0 g of R, 68.6 g of GP, and 120 g of EC were reacted using KOtBu as catalyst. 120 g of RGP3.4EO (205 mmol, 90.2%) were isolated as yellowish liquid. According to General Procedure 2 109 g of RGP3.4EO, 49.8 g of MA, 199 mg of HQME, 8.00 mg of PTZ, and 4.80 g of MSA were reacted using cyclohexane:toluene=70.0:30.0 as solvent. 126 g of RGP3.4EO-DMA (180 mmol, 93.3%) were isolated as yellowish oil: η=3.6 Pa*s, $n_D^{20}$=1.538.

Synthesis of RGP3.8EO-DMA (Inventive Example 4):

According to General Procedure 1 20.0 g of R, 54.9 g of GP, and 118 g of EC were reacted using KOH as catalyst. 102 g of RGP3.8EO (175 mmol, 96.3%) were isolated as yellowish liquid. According to General Procedure 2 102 g of RGP3.8EO, 45.6 g of MA, 185 mg of HQME, 7.40 mg of PTZ, and 6.30 g of MSA were reacted using cyclohexane:toluene=70.0:30.0 as solvent. 118 g of RGP3.8EO-DMA (165 mmol, 93.4%) were isolated as yellowish oil: η=3.3 Pa*s, $n_D^{20}$ 1.538.

Synthesis of BCGP2.5EO-DMA (Inventive Example 5):

According to General Procedure 1 33.4 g of BC, 63.7 g of GP, and 69.6 g of EC were reacted using KOH as catalyst. 114 g of BCGP2.5EO (192 mmol, 95.5%) were isolated as yellowish liquid. According to General Procedure 2 114 g of BCGP2.5EO, 49.5 g of MA, 204 mg of HQME, 8.20 mg of PTZ, and 7.00 g of MSA were reacted using cyclohexane:toluene=70.0:30.0 as solvent. 130.4 g of BCGP2.5EO-DMA (179 mmol, 93.5%) were isolated as yellowish oil: η=5.3 Pa*s, $n_D^{20}$=1.535.

Synthesis of PhloGP6EO-TMA (Inventive Example 6):

According to General Procedure 1 20.2 g of Phlo, 72.6 g of GP, and 141 g of EC were reacted using KOH as catalyst. 119 g of PhloGP6EO (142 mmol, 88.4%) were isolated as yellowish liquid. According to General Procedure 2 70.6 g of PhloGP6EO, 32.5 g of MA, 516 mg of HQME, 15.5 mg of PTZ, and 3.09 g of MSA were reacted using cyclohexane:toluene=20.0:80.0 as solvent. 83.2 g of PhloGP6EO-TMA (79.6 mmol, 94.8%) were isolated as yellowish oil: η=14.6 Pa*s, $n_D^{20}$=1.538.

Synthesis of PhloGP6EO-TA (Inventive Example 7):

According to General Procedure 1 20.2 g of Phlo, 72.6 g of GP, and 141 g of EC were reacted using KOH as catalyst. 119 g of PhloGP6EO (142 mmol, 88.4%) were isolated as yellowish liquid. According to General Procedure 2 87.1 g of PhloGP6EO, 33.6 g of AA, 603 mg of HQME, 18.1 mg of PTZ, and 3.70 g of MSA were reacted using cyclohexane:toluene=20.0:80.0 as solvent. 95.6 g of PhloGP6EO-TA (95.3 mmol, 92.0%) were isolated as yellowish oil: η=30.3 Pa*s, $n_D^{20}$=1.543.

Certain properties of the components which were synthesized are given in Table 2.

TABLE 2

| Component | Molecular Weight | Viscosity (Pa*s) | Refractive Index |
|---|---|---|---|
| CE1 | 634.7 | 9.4 | 1.542 |
| CE2 | 606.7 | 18.8 | 1.547 |
| IE1 | 634.7 | 5.5 | 1.542 |
| IE2 | 695.1 | 3.8 | 1.538 |
| IE3 | 703.0 | 3.6 | 1.538 |
| IE4 | 716.7 | 3.3 | 1.538 |
| IE5 | 727.41 | 5.3 | 1.535 |
| IE6 | 1045.2 | 14.6 | 1.538 |
| IE7 | 1003.1 | 30.3 | 1.543 |

The inventive polymerizable components are low viscous, have a sufficiently high refractive index and do not contain a bisphenol-A moiety.

Synthesis of Light Curing One Component Compositions

Some of the compounds synthesized were used for producing a (dental) composition. The compositions produced and tested with respect to their mechanical properties are given in Table 3 below. In Table 3 the values of the components a) to i) represent %-weight of the individual components in the corresponding formulation.

General Procedure A:

With magnetic stirring and under the exclusion of light the initiator system components were dissolved within the monomers at temperatures not above 50° C. (depending on the intrinsic viscosity of the used monomers).

General Procedure B:

According to General Procedure A the initiator system components were dissolved within the monomers. Under the exclusion of light and using a two-arm kneader the filler was mixed in portions with this mixture of initiator system and monomers. The amount of filler was manually determined depending on the desired handling properties of the dental composition. The dental composition was then light cured using an 800 mW halogen curing light (3M Oral Care, Elipar™ Trilight) and tested according to the corresponding measurements listed above. The respective values are given in Tables 3.

Composition A contains component a) but not compound (A) according to the invention. In Table 2 below, compound (A) is represented by components b) to e). Thus, Composition A can be considered as comparative example, whereas Compositions B to E can be considered as inventive examples.

TABLE 3

| | Dental Composition | | | | | |
|---|---|---|---|---|---|---|
| | A | B* | C* | D* | E* | F* |
| a) | 19.6 | | | | | |
| b) | | 18.7 | | | | |
| c) | | | 18.7 | | | |
| d) | | | | 18.7 | | |
| e) | | | | | 18.7 | |
| f) | | | | | | 18.7 |
| g) | 0.03 | 0.03 | 0.03 | 0.03 | 0.03 | 0.03 |
| h) | 0.19 | 0.19 | 0.19 | 0.19 | 0.19 | 0.19 |
| i) | 0.09 | 0.09 | 0.09 | 0.09 | 0.09 | 0.09 |
| j) | 80.1 | 81.0 | 81.0 | 81.0 | 81.0 | 81.0 |
| FS [MPa] | 137 ± 14.0 | 156 ± 8.00 | 168 ± 15.0 | 166 ± 12.0 | 169 ± 9.00 | 139 ± 6.00 |
| EM [GPa] | 10.0 ± 0.30 | 13.4 ± 0.90 | 12.7 ± 0.50 | 12.9 ± 0.70 | 12.8 ± 0.60 | 12.5 ± 0.40 |
| DoC [mm] | 4.81 | 4.46 ± 0.05 | 4.64 ± 0.13 | 4.29 ± 0.08 | 4.73 ± 0.02 | 4.58 ± 0.14 |
| Cusp-D [μm] | 9.40 ± 0.60 | 10.5 ± 0.40 | 10.4 ± 0.20 | 10.3 ± 0.20 | 10.7 ± 0.30 | 7.50 ± 0.20 |
| SHR [%] | 1.65 ± 0.06 | 1.60 ± 0.07 | 1.63 ± 0.02 | 1.69 ± 0.08 | 1.65 ± 0.02 | 1.45 ± 0.02 |
| DTS [MPa] | 74.0 ± 7.70 | 87.9 ± 3.60 | 92.9 ± 6.60 | 91.9 ± 3.80 | 93.5 ± 7.40 | 67.0 ± 6.00 |

*inventive examples

As can be seen, compositions containing compound (A1) according to the invention are either superior with respect to certain properties (e.g. FS, EM, DTS) compared to compositions not containing compound (A1) according to the invention, or show otherwise adequate properties on a high level (e.g. DoC, SHR, Cusp-D).

The invention claimed is:

1. A dental composition comprising
   a) a resin matrix,
   b) an initiator system,
   c) a filler system,
   the resin matrix comprising a polymerizable component A1 being characterized by either of the following formulas (I), (II) or (III)

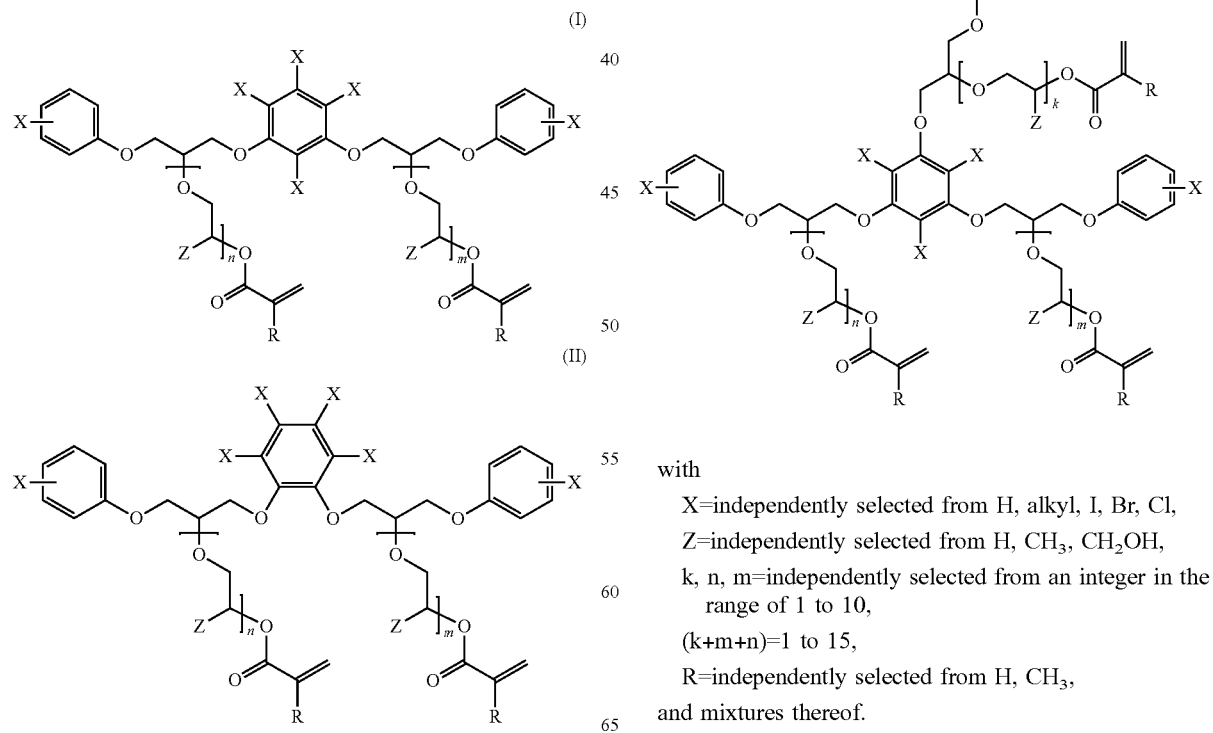

with
   X=independently selected from H, alkyl, I, Br, Cl,
   Z=independently selected from H, $CH_3$, $CH_2OH$,
   n, m=independently selected from an integer in the range of 1 to 10,
   (m+n)=1 to 10,
   R=independently selected from H, $CH_3$, with
   X=independently selected from H, alkyl, I, Br, Cl,
   Z=independently selected from H, $CH_3$, $CH_2OH$,
   k, n, m=independently selected from an integer in the range of 1 to 10,
   (k+m+n)=1 to 15,
   R=independently selected from H, $CH_3$,
   and mixtures thereof.

2. The dental composition according to claim 1, polymerizable component A1 being selected from

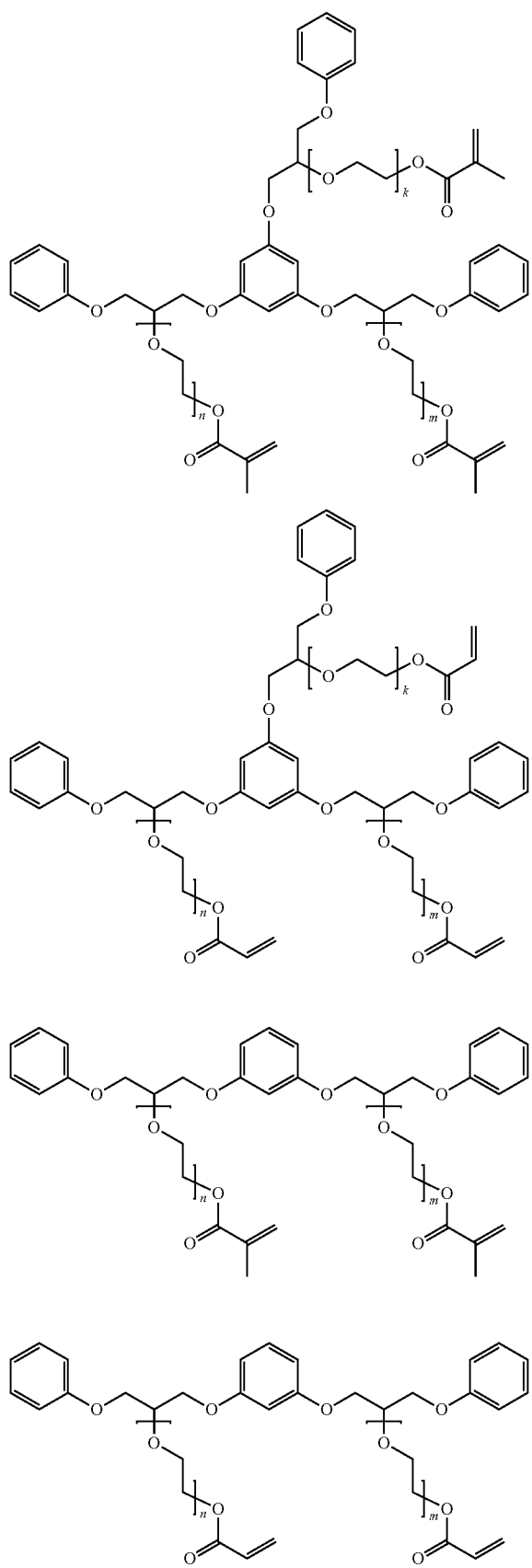

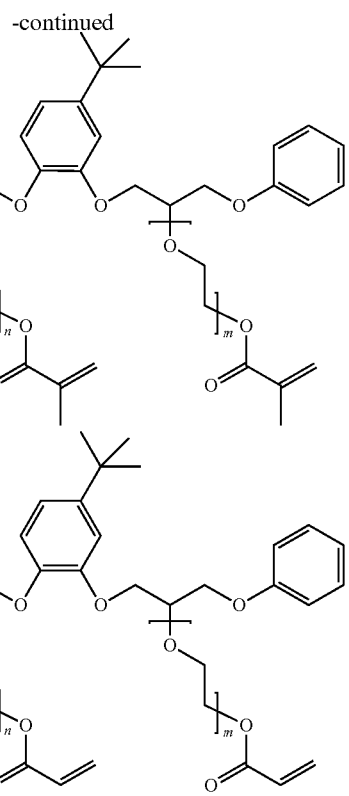

-continued with m, n, k=independently selected from an integer in the range of 1 to 10, and (m+n)=1 to 10, or (m+n+k)=1 to 15, and mixtures thereof.

3. The dental composition according to claim 1, polymerizable component A1 being characterized by the following properties alone or in combination:

a) viscosity: 2 to 40 Pa*s at 23° C. and a shear rate of 100 $s^{-1}$ using a 25 mm/1° cone/plate system;

b) refractive index: 1.520 to 1.565 measured at 20.0° C. at a wavelength of 589 nm.

4. The dental composition according to claim 1, the resin matrix comprising one or more polymerizable components A2 being different from polymerizable component A1, the polymerizable component A2 being preferably characterized by the following formula:

$$A_nBA_m$$

with A being an ethylenically unsaturated group,

B being selected from (i) linear or branched $C_1$ to $C_{12}$ alkyl, optionally substituted with halogenides, or OH (ii) $C_6$ to $C_{12}$ aryl, optionally substituted with halogenides or OH, or (iii) organic group having 4 to 20 carbon atoms bonded to one another by one or more ether, thioether, ester, thioester, thiocarbonyl, amide, urethane, carbonyl and/or sulfonyl linkages, m, n being independently selected from 0, 1, 2, 3, 4, 5 or 6 with the proviso that n+m is greater 0.

5. The dental composition according to claim 1, the initiator system comprising a photo initiator system, preferably a photo initiator system comprising a ketone sensitizer, an amine donor and optionally an iodonium salt.

6. The dental composition according to claim 1, the filler system comprising a nano-sized particles and being present in an amount of 20 to 90 wt. % with respect to the weight of the whole composition.

7. The dental composition according to claim 1 comprising the components in the following amounts:
   a) polymerizable component A1: 3 to 50 wt. %,
   b) polymerizable component A2: 0 to 60 wt. %,
   c) initiator system: 0.1 to 4 wt. %,
   d) filler system: 20 to 90 wt. %,
   e) plasticiser: 0 to 20 wt. %,
   f) adjuvants: 0 to 15 wt. %,
   wt. % with respect to the weight of the whole composition.

8. The dental composition according to claim 1 not comprising the following components alone or in combination:
   solvents having a boiling point below 150° C. in an amount of 5 wt. % or more;
   Bis-phenol A derived components in an amount of 2 wt. % or more;
   polymerizable components comprising an acidic moiety in an amount of 2 wt. % or more, wt. % with respect to the weight of the whole composition.

9. The dental composition according to claim 1, the dental composition being characterized by the following features alone or in combination before hardening:
   a) Viscosity: 5 to 100 Pa*s at 25° C. and a shear rate of 100 s$^{-1}$,
   b) pH-value: 6 to 8;
   c) hardenable within 10 min after irradiation with light having a wavelength in the range of 400 to 700 nm.

10. The dental composition according to claim 1, the dental composition being characterized by the following features alone or in combination after hardening:
    a) Flexural strength: 140 to 200 Mpa*s determined according to ISO 4049 (2019);
    b) E-Modulus (EM): 4 to 16 GPa determined according to ISO 4049 (2019);
    c) depth of cure: 3 to 7 mm determined according to ISO 4049 (2019);
    d) bonded disk shrinkage-strain: 1.50 to 1.80% determined as described in the experimental section;
    e) diametral Tensile Strength: 75 to 100 MPa determined according to ISO 7489 (2019);
    f) cusp deflection: <12 μm.

11. The dental composition according to claim 1, the dental composition being characterized by comprising:
    a) polymerizable component A1 in an amount of 3 to 50 wt. %,
    b) polymerizable component A2 in an amount of 0 to 60 wt. %,
    c) initiator system in an amount of 0.1 to 4 wt. %, the initiator system comprising a ketone sensitizer and an amine donor,
    d) filler system comprising nano-sized particles in an amount of 20 to 90 wt. %,
    e) plasticiser in an amount of 0 to 20 wt. %,
    f) adjuvants in an amount of 0 to 15 wt. %,
    wt. % with respect to the weight of the whole composition,
    the composition not comprising a bis-phenol A moiety containing component in an amount of 5 wt. % or more.

12. A kit of parts comprising the dental composition according to claim 1 and the following items alone or in combination: dental adhesive; dental primer; dispensing device; polishing equipment; dental curing light.

* * * * *